(12) United States Patent
Ackermann et al.

(10) Patent No.: US 7,405,236 B2
(45) Date of Patent: Jul. 29, 2008

(54) INDOLE DERIVATIVES COMPRISING AN ACETYLENE GROUP

(75) Inventors: Jean Ackermann, Riehen (CH); Johannes Aebi, Basel (CH); Alfred Binggeli, Binningen (CH); Uwe Grether, Efringen-Kirchen (DE); Bernd Kuhn, Liestal (CH); Hans-Peter Maerki, Basel (CH); Markus Meyer, Neuenburg (DE)

(73) Assignee: Hoffman-La Roche Inc., Nutley, NJ (US)

( * ) Notice: Subject to any disclaimer, the term of this patent is extended or adjusted under 35 U.S.C. 154(b) by 543 days.

(21) Appl. No.: 11/195,206

(22) Filed: Aug. 2, 2005

(65) Prior Publication Data

US 2006/0035956 A1 Feb. 16, 2006

(30) Foreign Application Priority Data

Aug. 16, 2004 (EP) .................................. 04019378

(51) Int. Cl.
*A61K 31/404* (2006.01)
*C07D 209/04* (2006.01)

(52) U.S. Cl. ...................... 514/415; 548/469; 548/509; 548/510

(58) Field of Classification Search ................ 548/469, 548/509, 510; 514/415
See application file for complete search history.

(56) References Cited

U.S. PATENT DOCUMENTS

| 4,378,368 | A | 3/1983 | Cassady et al. | |
|---|---|---|---|---|
| 6,890,947 | B2 * | 5/2005 | Binggeli et al. | 514/414 |
| 6,995,263 | B2 * | 2/2006 | Ackermann et al. | 544/333 |
| 7,253,192 | B2 * | 8/2007 | Ackermann et al. | 514/342 |
| 7,265,149 | B2 * | 9/2007 | Ackermann et al. | 514/414 |

FOREIGN PATENT DOCUMENTS

| EP | 1380562 A1 | 1/2004 |
|---|---|---|
| EP | 1394147 A1 | 3/2004 |
| WO | WO 03/074051 A1 | 9/2003 |
| WO | WO 2004/063190 A1 | 7/2004 |

OTHER PUBLICATIONS

Oliver et al; Proc Nat Acad Sci USA 2001; 98: 5306-11.
Guerre-Millo et al; J Biol Chem 2000; 275: 16638-16642.
Natchus, Michael G, et. al.,Journal of Medicinal Chemistry (2001), 44(7), 1060-1071.
M. Matsumoto, N. Watanabe, *Heterocycles* 1987, 26, 913-916.
E. Piers, V. B. Haarstadt, R. J. Cushley, R. K. Brown, *Canadian Journal of Chemistry* 1962, 40, 511-517.
J. Labeled Compounds & Radiopharmaceuticals 43(7), 683-691, (2000).
Tetrahedron Letters 43(42), 7617-7619(2002).
Belostotskii, Anatoly M., Hassner, A., *Tetrahedron Lett.* 1994, 35(28), 5075-6.
Loibner, H., Pruckner, A., Stuetz, A., *Tetrahedron Lett.* 1984, 25, 2535-2536.
Stara, Irena G, et. al,. Chem. Commun. (1999), 64(4), 649-672.
Thorand, Stephan; Krause, Norbert Journal of Organic Chemistry (1998), 63(23), 8551-8553.

* cited by examiner

*Primary Examiner*—Golam M Shameem
(74) *Attorney, Agent, or Firm*—George W. Johnston; Dennis P. Tramaloni; Samuel H. Megerditchain

(57) ABSTRACT

This invention is directed to compounds of the formula (I):

wherein one of $R^6$, $R^7$, $R^8$ and $R^9$ is and X, $R^1$ to $R^{12}$, m, n and o are as defined in the description, and pharmaceutically acceptable salts and/or esters thereof. The invention is also directed to pharmaceutical compositions containing such compounds, to a process for their preparation and to their use for the treatment and/or prevention of diseases which are modulated by PPARδ and/or PPARα agonists.

25 Claims, No Drawings

INDOLE DERIVATIVES COMPRISING AN ACETYLENE GROUP

FIELD OF THE INVENTION

The present invention is directed to novel indolyl derivatives of the formula (I):

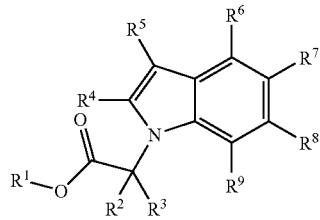

and pharmaceutically acceptable salts and esters thereof.

It has been found that compounds of formula I are useful as lipid modulators and insulin sensitizers. In particular, compounds of formula I are PPAR activators.

All documents cited or relied upon below are expressly incorporated herein by reference.

BACKGROUND OF THE INVENTION

Peroxisome Proliferator Activated Receptors (PPARs) are members of the nuclear hormone receptor superfamily. The PPARs are ligand-activated transcription factors that regulate gene expression and control multiple metabolic pathways. Three subtypes have been described: PPARα, PPARδ (also known as PPARβ, and PPARγ. PPARδ is ubiquitously expressed. PPARα is predominantly expressed in the liver, kidney and heart. There are at least two major isoforms of PPARγ. PPARγ1 is expressed in most tissues, and the longer isoform, PPARγ2 is almost exclusively expressed in adipose tissue. The PPARs modulate a variety of physiological responses including regulation of glucose- and lipid-homeostasis and metabolism, energy balance, cell differentiation, inflammation and cardiovascular events.

Approximately half of all patients with coronary artery disease have low concentrations of plasma HDL cholesterol. The atheroprotective function of HDL was first highlighted almost 25 years ago and stimulated exploration of the genetic and environmental factors that influence HDL levels. The protective function of HDL comes from its role in a process termed reverse cholesterol transport. HDL mediates the removal of cholesterol from cells in peripheral tissues including those in the atherosclerotic lesions of the arterial wall. HDL then delivers its cholesterol to the liver and sterol-metabolizing organs for conversion to bile and elimination. Data from the Framingham study showed that HDL-C levels are predictive of coronary artery disease risk independently of LDL-C levels. The estimated age-adjusted prevalence among Americans age 20 and older who have HDL-C of less than 35 mg/dl is 16% (males) and 5.7% (females). A substantial increase of HDL-C is currently achieved by treatment with niacin in various formulations. However, the substantial side-effects limit the therapeutic potential of this approach.

As many as 90% of the 14 million diagnosed type 2 diabetic patients in the US are overweight or obese, and a high proportion of type 2 diabetic patients have abnormal concentrations of lipoproteins. The prevalence of total cholesterol>240 mg/dl is 37% in diabetic men and 44% in women. The respective rates for LDL-C>160 mg/dl are 31% and 44%, respectively, and for HDL-C<35 mg/dl 28% and 11%, respectively. Diabetes is a disease in which a patient's ability to control glucose levels in blood is decreased because of partial impairment in response to the action of insulin. Type II diabetes (T2D) is also called non-insulin dependent diabetes mellitus (NIDDM) and afflicts 80-90% of all diabetic patients in developed countries. In T2D, the pancreatic Islets of Langerhans continue to produce insulin. However, the target organs for insulin action, mainly muscle, liver and adipose tissue, exhibit a profound resistance to insulin stimulation. The body continues to compensate by producing unphysiologically high levels of insulin, which ultimately decreases in later stage of disease, due to exhaustion and failure of pancreatic insulin-producing capacity. Thus T2D is a cardio-vascular-metabolic syndrome associated with multiple comorbidities including insulin resistance, dyslipidemia, hypertension, endothelial dysfunction and inflammatory atherosclerosis.

First line treatment for dyslipidemia and diabetes generally involves a low-fat and low-glucose diet, exercise and weight loss. However, compliance can be moderate, and as the disease progresses, treatment of the various metabolic deficiencies becomes necessary with e.g. lipid-modulating agents such as statins and fibrates for dyslipidemia and hypoglycemic drugs, e.g. sulfonylureas or metformin for insulin resistance. A promising new class of drugs has recently been introduced that resensitizes patients to their own insulin (insulin sensitizers), thereby restoring blood glucose and triglyceride levels to normal, and in many cases, obviating or reducing the requirement for exogenous insulin. Pioglitazone (Actos™) and rosiglitazone (Avandia™) belong to the thiazolidinedione (TZD) class of PPARγ-agonists and were the first in their class to be approved for NIDDM in several countries. These compounds, however, suffer from side effects, including rare but severe liver toxicity (as seen with troglitazone). They also increase body weight in patients.

Therefore, new, more efficacious drugs with greater safety and lower side effects are urgently needed. Recent studies provide evidence that agonism of PPARδ would result in compounds with enhanced therapeutic potential, i.e. such compounds should improve the lipid profile, with a superior effect on HDL-C raising compared to current treatments and with additional positive effects on normalization of insulin-levels (Oliver et al; Proc Nat Acad Sci USA 2001; 98: 5306-11). Recent observations also suggest that there is a independent PPARα mediated effect on insulin-sensitization in addition to its well known role in reducing triglycerides (Guerre-Millo et al; J Biol Chem 2000; 275: 16638-16642). Thus selective PPARδ agonists or PPARδ agonists with additional PPARα activity may show superior therapeutic efficacy without the side-effects such as the weight gain seen with PPARγ agonists.

SUMMARY OF THE INVENTION

In one embodiment of the present invention, provided is a compound of the formula (I):

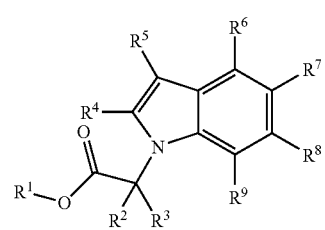

wherein:

$R^1$ is hydrogen or $C_{1-7}$-alkyl;

$R^2$ and $R^3$ independently from each other are selected from the group consisting of hydrogen, $C_{1-7}$-alkyl and $C_{1-7}$-alkyl-$C_{1-7}$-alkoxy;

$R^4$ and $R^5$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-aklyl, fluoro-$C_{1-7}$-alkoxy, cyano-$C_{1-7}$-alkyl and cyano;

$R^6$, $R^7$, $R^8$ and $R^9$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, fluoro-$C_{1-7}$-alkoxy, cyano-$C_{1-7}$-alkyl and cyano;

and one of $R^6$, $R^7$, $R^8$ and $R^9$ is

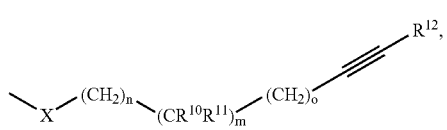

wherein:

X is selected from the group consisting of S, O, $NR^{13}$, $(CH_2)_P NR^{13}CO$ and $(CH_2)_P CONR^{13}$, $R^{13}$ is selected from the group consisting of hydrogen, $C_{1-7}$-alkyl, $C_{3-7}$-cycloalkyl, fluoro-$C_{1-7}$-alkyl, hydroxy-$C_{2-7}$-alkyl and $C_{1-7}$-alkoxy-$C_{2-7}$-alkyl;

$R^{10}$ is selected from the group consisting of $C_{1-7}$-alkyl, $C_{3-7}$-cycloalkyl, fluoro-$C_{1-7}$-alkyl and $C_{1-7}$-alkoxy-$C_{1-7}$-alkyl;

$R^{11}$ is selected from the group consisting of hydrogen, $C_{1-7}$-alkyl and $C_{1-7}$-alkoxy-$C_{1-7}$-alkyl;

or $R^{10}$ and $R^{11}$ together with the carbon atom they are attached to form a $C_{3-6}$-cycloalkyl ring; $R^{12}$ is aryl or heteroaryl;

m, o, p is 0, 1 or 2; n is 0, 1, 2 or 3 and the sum of m, n and o is 1 to 5; and pharmaceutically acceptable salts and/or esters thereof.

In another embodiment of the present invention, provided is a process for the manufacture of a compound according to formula I, comprising the steps of: reacting a compound of formula

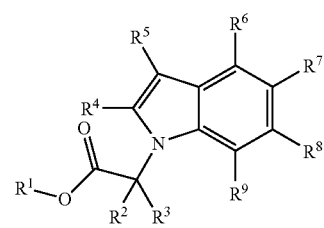

II wherein $R^1$ is $C_{1-7}$-alkyl, $R^2$ to $R^9$ are as defined in claim 1 and one of $R^6$, $R^7$, $R^8$ or $R^9$ is selected from —OH, —SH or —$NHR^{13}$, wherein $R^{13}$ is as defined in claim 1, with a compound of formula

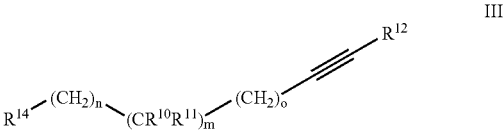

III wherein $R^{10}$, $R^{11}$, $R^{12}$ n, m and o are as defined in claim 1 and $R^{14}$ is —OH, —Cl, —Br, —I or another leaving group, to obtain a compound of formula

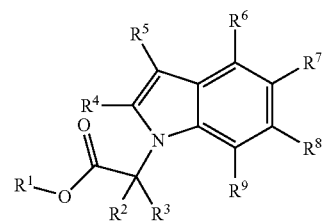

I-1 wherein one of $R^6$, $R^7$, $R^8$ and $R^9$ is

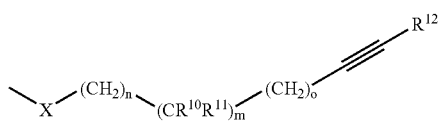

and wherein X is O, S, or —$NR^{13}$, $R^1$ is $C_{1-7}$-alkyl and $R^2$ to $R^{13}$ are as defined in claim 1, and optionally hydrolyzing the ester group to obtain a compound of formula I, wherein $R^1$ is hydrogen;

or, alternatively, reacting a compound of formula

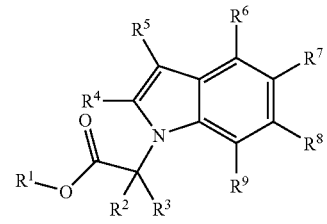

IV wherein $R^1$ is $C_{1-7}$-alkyl, $R^2$ to $R^9$ are as defined in claim 1 and one of $R^6$, $R^7$, $R^8$ or $R^9$ is —$(CH_2)_p$—$NHR^{13}$, wherein $R^{13}$ and p are as defined in claim 1, with a compound of formula

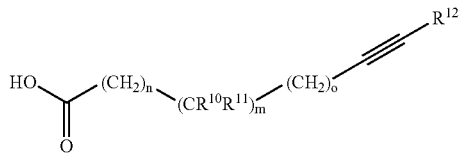

V wherein $R^{10}$, $R^{11}$, $R^{12}$, m, n and o are as defined in claim 1, to obtain a compound of formula

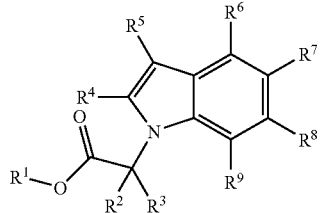

wherein one of $R^6$, $R^7$, $R^8$ and $R^9$ is

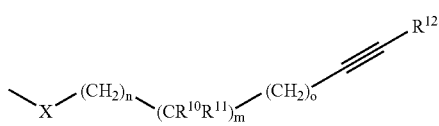

and wherein X is $-(CH_2)_p-NR^{13}CO-$, $R^1$ is $C_{1-7}$-alkyl and $R^2$ to $R^{13}$ and m, n, o and p are as defined in claim 1, and optionally hydrolyzing the ester group to obtain a compound of formula I, wherein $R^1$ is hydrogen;

or, alternatively, reacting a compound of formula

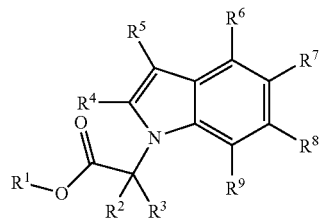

wherein $R^1$ is $C_{1-7}$-alkyl, $R^2$ to $R^9$ are as defined in claim 1 and one of $R^6$, $R^7$, $R^8$ or $R^9$ is $-(CH_2)_p-COOH$, and p is defined as defined in claim 1, with a compound of formula

VII

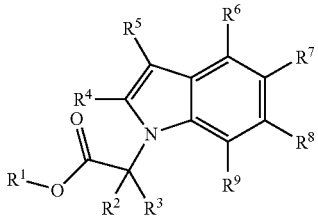

wherein $R^{10}$, $R^{11}$, $R^{12}$, $R^{13}$, m, n and o are as defined in claim 1, to obtain a compound of formula

I-3

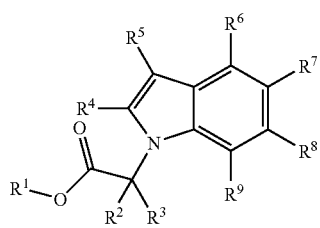

wherein one of $R^6$, $R^7$, $R^8$ and $R^9$ is

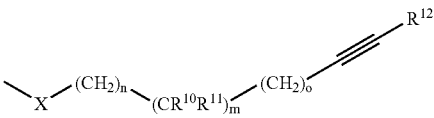

and wherein X is $-(CH_2)_p-CONR^{13}$, $R^1$ is $C_{1-7}$-alkyl and $R^2$ to $R^{13}$ and m, n, o and p are as defined in claim 1, and optionally hydrolyzing the ester group to obtain a compound of formula I, wherein $R^1$ is hydrogen;

or, alternatively, reacting a compound of formula

VIII

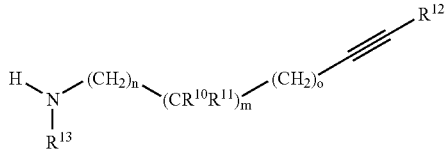

wherein $R^4$ to $R^9$ are as defined in claim 1, with a compound of formula

IX

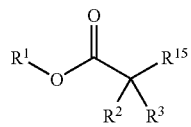

wherein $R^1$ is $C_{1-7}$-alkyl, $R^2$ and $R^3$ are as defined in claim 1 and $R^{15}$ is halogen, triflate or another leaving group, to obtain a compound of formula

I

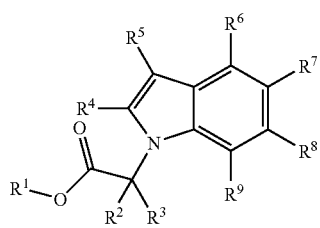

wherein $R^1$ is $C_{1-7}$-alkyl and $R^2$ to $R^9$ are as defined in claim 1, and optionally hydrolyzing the ester group to obtain a compound of formula I, wherein $R^1$ is hydrogen.

In a further embodiment of the present invention, provided is a pharmaceutical composition comprising a therapeutically effective amount of a compound of the formula I as well as a pharmaceutically acceptable carrier and/or adjuvant.

In a yet another embodiment of the present invention, provided is a method for the treatment and/or prevention of diseases which are modulated by PPARδ and/or PPARα agonists, comprising the step of administering a therapeutically effective amount of a compound according to formula I to a human being or animal in need thereof.

DETAILED DESCRIPTION

The novel compounds of the present invention exceed the compounds known in the art, inasmuch as they, for example, bind to and selectively activate PPARδ or coactivate PPARδ and PPARα simultaneously and very efficiently, and with much improved pharmacokinetic properties. Therefore, these compounds combine the anti-dyslipidemic and anti-glycemic effects of PPARδ and PPARα activation with no effect on PPARγ. Consequently, HDL cholesterol is increased, triglycerides lowered and plasma glucose and insulin are reduced. In addition, such compounds may also lower LDL cholesterol, decrease blood pressure and counteract inflammatory atherosclerosis. Furthermore, such compounds may also be useful for treating inflammatory diseases such as rheumatoid arthritis, osteoarthritis, and psoriasis. Since multiple facets of combined dyslipidemia and the T2D disease syndrome are addressed by PPARδ-selective agonists and PPARδ and α coagonists, they are expected to have an enhanced therapeutic potential compared to the compounds already known in the art.

The compounds of the present invention further exhibit improved pharmacological properties compared to known compounds.

Unless otherwise indicated the following definitions are set forth to illustrate and define the meaning and scope of the various terms used to describe the invention herein.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_{1-7}$-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the groups specifically exemplified herein.

The term "halogen" refers to fluorine, chlorine, bromine and iodine.

The term "fluoro-lower alkyl" or "fluoro-$C_{1-7}$-alkyl" refers to lower alkyl groups which are mono- or multiply substituted with fluorine. Examples of fluoro-lower alkyl groups are e.g. —$CF_3$, —$CH_2CF_3$, —$CH(CF_3)_2$ and the groups specifically exemplified herein.

The term "alkoxy" refers to the group R'—O—, wherein R' is alkyl. The term "lower-alkoxy" or "$C_{1-7}$-alkoxy" refers to the group R'—O—, wherein R' is lower-alkyl. Examples of lower-alkoxy groups are e.g. methoxy, ethoxy, propoxy, isopropoxy, butoxy, isobutoxy and hexyloxy. Preferred are the lower-alkoxy groups specifically exemplified herein.

The term "fluoro-lower alkoxy" or "fluoro-$C_{1-7}$-alkoxy" refers to lower alkoxy groups which are mono- or multiply substituted with fluorine. Examples of fluoro-lower alkoxy groups are e.g. —$OCF_3$, —$OCH_2CF_3$, —O—$CH(CF_3)_2$ and the groups specifically exemplified herein.

The term "lower alkenyl" or "$C_{2-7}$-alkenyl", alone or in combination, signifies a straight-chain or branched hydrocarbon residue comprising an olefinic bond and up to 7, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl.

The term "lower alkinyl" or "$C_{2-7}$-alkinyl", alone or in combination, signifies a straight-chain or branched hydrocarbon residue comprising a triple bond and up to 7, preferably up to 6, particularly preferred up to 4 carbon atoms. Examples of alkinyl groups are ethinyl, 1-propinyl, or 2-propinyl.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl.

The term "aryl" relates to the phenyl or naphthyl group, preferably the phenyl group, which can optionally be mono- or multiply-substituted, particularly mono- or di-substituted by halogen, hydroxy, CN, $CF_3$, $NO_2$, $NH_2$, N(H, lower-alkyl), N(lower-alkyl)$_2$, carboxy, aminocarbonyl, lower-alkyl, lower fluoro-alkyl, lower-alkoxy, lower fluoro-alkoxy, aryl and/or aryloxy. Preferred substituents are halogen, $CF_3$, $OCF_3$, lower-alkyl and/or lower-alkoxy. Preferred are the specifically exemplified aryl groups.

The term "heteroaryl" refers to an aromatic 5- or 6-membered ring which can comprise 1, 2 or 3 atoms selected from nitrogen, oxygen and/or sulphur such as furyl, pyridyl, 1,2-, 1,3- and 1,4-diazinyl, thienyl, isoxazolyl, oxazolyl, imidazolyl, or pyrrolyl. The term "heteroaryl" further refers to bicyclic aromatic groups comprising two 5- or 6-membered rings, in which one or both rings can contain 1, 2 or 3 atoms selected from nitrogen, oxygen or sulphur such as e.g. indole or quinoline, or partially hydrogenated bicyclic aromatic groups such as e.g. indolinyl. A heteroaryl group may have a substitution pattern as described earlier in connection with the term "aryl". Preferred heteroaryl groups are e.g. thienyl and furyl which can optionally be substituted as described above, preferably with halogen, $CF_3$, $OCF_3$, lower-alkyl and/or lower-alkoxy.

The term "protecting group" refers to groups such as e.g. acyl, alkoxycarbonyl, aryloxycarbonyl, silyl, or imine-derivatives, which are used to temporarily block the reactivity of functional groups. Well known protecting groups are e.g. t-butyloxycarbonyl, benzyloxycarbonyl, fluorenylmethyloxycarbonyl or diphenylmethylene which can be used for the protection of amino groups, or lower-alkyl-, β-trimethylsilylethyl- and β-trichloroethyl-esters, which can be used for the protection of carboxy groups.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

The term "pharmaceutically acceptable salts" embraces salts of the compounds of formula (I) with pharmaceutically acceptable bases such as alkali salts, e.g. Na- and K-salts, alkaline earth salts, e.g. Ca- and Mg-salts, and ammonium or substituted ammonium salts, such as e.g. trimethylammonium salts. The term "pharmaceutically acceptable salts" also relates to such salts.

The compounds of formula (I) can also be solvated, e.g. hydrated. The solvation can be effected in the course of the manufacturing process or can take place e.g. as a consequence of hygroscopic properties of an initially anhydrous compound of formula (I) (hydration). The term pharmaceutically acceptable salts also includes pharmaceutically acceptable solvates.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The methyl and ethyl esters are especially preferred. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

In detail, the present invention relates to compounds of formula (I)

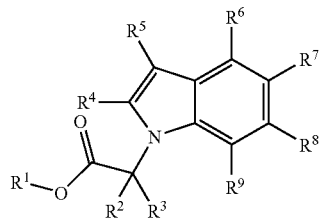

I wherein $R^1$ is hydrogen or $C_{1-7}$-alkyl;

$R^2$ and $R^3$ independently from each other are selected from the group consisting of hydrogen, $C_{1-7}$-alkyl and $C_{1-7}$-alkyl-$C_{1-7}$-alkoxy;

$R^4$ and $R^5$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, fluoro-$C_{1-7}$-alkoxy, cyano-$C_{1-7}$-alkyl and cyano;

$R^6$, $R^7$, $R^8$ and $R^9$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, fluoro-$C_{1-7}$-alkoxy, cyano-$C_{1-7}$-alkyl and cyano;

and one of $R^6$, $R^7$, $R^8$ and $R^9$ is

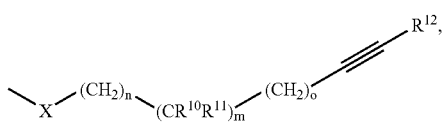

wherein

X is selected from the group consisting of S, O, $NR^{13}$, $(CH_2)_p NR^{13}CO$ and $(CH_2)_p CONR^{13}$, $R^{13}$ is selected from the group consisting of hydrogen, $C_{1-7}$-alkyl, $C_{3-7}$-cycloalkyl, fluoro-$C_{1-7}$-alkyl, hydroxy-$C_{2-7}$-alkyl and $C_{1-7}$-alkoxy-$C_{2-7}$-alkyl;

$R^{10}$ is selected from the group consisting of $C_{1-7}$-alkyl, $C_{3-7}$-cycloalkyl, fluoro-$C_{1-7}$-alkyl and $C_{1-7}$-alkoxy-$C_{1-7}$-alkyl;

$R^{11}$ is selected from the group consisting of hydrogen, $C_{1-7}$-alkyl and $C_{1-7}$-alkoxy-$C_{1-7}$-alkyl;

or $R^{10}$ and $R^{11}$ together with the carbon atom they are attached to form a $C_{3-6}$-cycloalkyl ring;

$R^{12}$ is aryl or heteroaryl;

m, o, p is 0, 1 or 2; n is 0, 1, 2 or 3 and the sum of m, n and o is 1 to 5; and pharmaceutically acceptable salts and/or esters thereof.

Preferred compounds of formula I of the present invention are compounds of formula

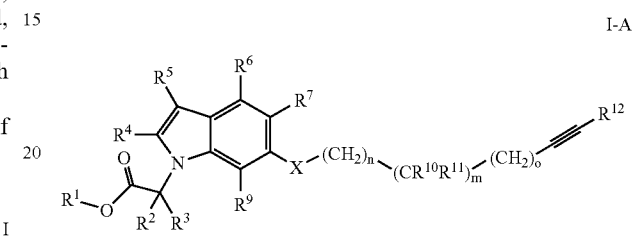

I-A wherein

X, $R^1$ to $R^5$, $R^{10}$ to $R^{12}$, m, n and o are as defined herein before;

$R^6$, $R^7$ and $R^9$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, fluoro-$C_{1-7}$-alkoxy, cyano-$C_{1-7}$-alkyl and cyano; and pharmaceutically acceptable salts and/or esters thereof.

More preferred are those compounds of formula I-A in accordance with the present invention, wherein $R^6$, $R^7$ and $R^9$ are hydrogen.

Also preferred are compounds of formula I having the formula

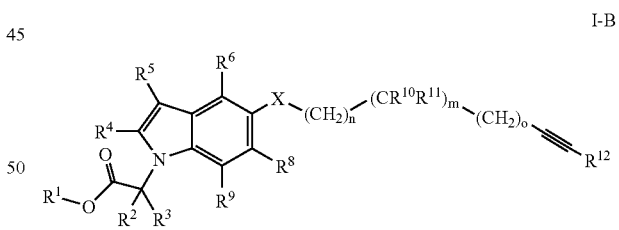

I-B wherein

X, $R^1$ to $R^5$, $R^{10}$ to $R^{12}$, m, n and o are as defined herein before;

$R^6$, $R^8$ and $R^9$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, fluoro-$C_{1-7}$-alkoxy, cyano-$C_{1-7}$-alkyl and cyano; and pharmaceutically acceptable salts and/or esters thereof.

Especially preferred are compounds of formula I-B, wherein $R^6$, $R^8$ and $R^9$ are hydrogen.

Also preferred compounds of formula I have the formula

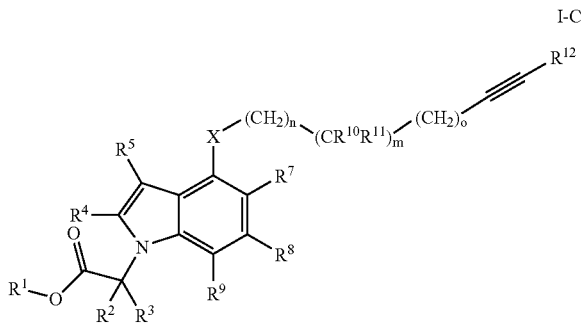

I-C wherein
X, $R^1$ to $R^5$, $R^{10}$ to $R^{12}$, m, n and o are as defined herein before;
$R^7$, $R^8$ and $R^9$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, fluoro-$C_{1-7}$-alkoxy, cyano-$C_{1-7}$-alkyl and cyano; and pharmaceutically acceptable salts and/or esters thereof.

More preferred are those compounds of formula I-C, wherein $R^7$, $R^8$ and $R^9$ are hydrogen.

Further preferred compounds of formula I have the formula

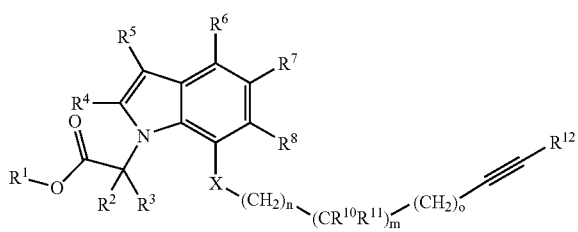

I-D wherein
X, $R^1$ to $R^5$, $R^{10}$ to $R^{12}$, m, n and o are as defined herein before;
$R^6$, $R^7$ and $R^8$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, fluoro-$C_{1-7}$-alkoxy, cyano-$C_{1-7}$-alkyl and cyano; and pharmaceutically acceptable salts and/or esters thereof.

More preferred are those compounds of formula I-D, wherein $R^7$, $R^8$ and $R^9$ are hydrogen.

Furthermore, compounds of formula I, wherein $R^1$ is hydrogen, are preferred. Compounds of formula I, wherein $R^2$ and $R^3$ independently from each other are hydrogen or methyl, are also preferred. Especially preferred are compounds of formula I, wherein $R^2$ and $R^3$ are hydrogen.

Preferred are further compounds of formula I, wherein $R^4$ is hydrogen.

Compounds of formula I, wherein $R^5$ is hydrogen, $C_{1-7}$-alkyl or halogen, are also preferred. Especially preferred are compounds of formula I, wherein $R^5$ is hydrogen. Preferred are further compounds of formula I according to the present invention, wherein X is S, O or $NR^{13}$ and wherein $R^{13}$ is hydrogen, $C_{1-7}$-alkyl, $C_{3-7}$-cycloalkyl, fluoro-$C_{1-7}$-alkyl, hydroxy-$C_{2-7}$-alkyl, or $C_{1-7}$-alkoxy-$C_{2-7}$-alkyl.

More preferred are compounds of formula I, wherein X is S.

Especially preferred are compounds of formula I, wherein X is O.

In addition, compounds of formula I of the present invention, wherein X is $(CH_2)_p NR^{13}CO$ or $(CH_2)_p CONR^{13}$ and wherein $R^{13}$ is selected from hydrogen, $C_{1-7}$-alkyl, $C_{3-7}$-cycloalkyl, fluoro-$C_{1-7}$-alkyl, hydroxy-$C_{2-7}$-alkyl, or $C_{1-7}$-alkoxy-$C_{2-7}$-alkyl and p is 0, 1 or 2, are also preferred.

Especially preferred within this group are those compounds, wherein X is $(CH_2)_p NR^{13}CO$, $R^{13}$ is hydrogen or methyl and p is 0. Compounds, wherein X is $(CH_2)_p NR^{13}CO$, $R^{13}$ is hydrogen or methyl and p is 1, are also preferred.

The integer m is 0, 1 or 2. Especially preferred are compounds of formula I according to the present invention, wherein m is 0.

The integer n is 0, 1, 2 or 3, o is 0, 1 or 2, and p is 0, 1 or 2, with the proviso that the sum of m, n and o is 1 to 5.

Preferred are compounds of formula I, wherein m is 0 and the sum of n and o is 1, 2 or 3. Also preferred are compounds of formula I, wherein the sum of n and o is 2 or 3. Compounds of formula I, wherein $R^{12}$ is aryl, are preferred. More preferred are those compounds of formula I, wherein $R^{12}$ is unsubstituted phenyl or phenyl substituted with one to three groups selected from $C_{1-7}$-alkyl, $C_{1-7}$-alkoxy, halogen, fluoro-$C_{1-7}$-alkyl, fluoro-$C_{1-7}$-alkoxy and cyano, with those compounds, wherein $R^{12}$ is phenyl substituted with halogen, fluoro-$C_{1-7}$-alkyl or fluoro-$C_{1-7}$-alkoxy, being particularly preferred.

Examples of preferred compounds of formula I are the following:

{6-[5-(4-trifluoromethoxy-phenyl)-pent-4-ynyloxy]-indol-1-yl}-acetic acid,

{6-[5-(3-trifluoromethoxy-phenyl)-pent-4-ynyloxy]-indol-1-yl}-acetic acid,

{6-[5-(4-trifluoromethyl-phenyl)-pent-4-ynyloxy]-indol-1-yl}-acetic acid,

{6-[5-(3-trifluoromethyl-phenyl)-pent-4-ynyloxy]-indol-1-yl}-acetic acid,

{4-[5-(4-trifluoromethoxy-phenyl)-pent-4-ynyloxy]-indol-1-yl}-acetic acid,

{5-[5-(4-trifluoromethoxy-phenyl)-pent-4-ynyloxy]-indol-1-yl}-acetic acid,

{6-[2,2-dimethyl-5-(4-trifluoromethoxy-phenyl)-pent-4-ynyloxy]-indol-1-yl}-acetic acid, (6-{methyl-[5-(3-trifluoromethoxy-phenyl)-pent-4-ynoyl]-amino}-indol-1-yl)-acetic acid, {6-[5-(4-trifluoromethoxy-phenyl)-pent-4-ynylamino]-indol-1-yl}-acetic acid, (6-{methyl-[5-(4-trifluoromethoxy-phenyl)-pent-4-ynoyl]-amino}-indol-1-yl)-acetic acid, {7-[5-(4-trifluoromethoxy-phenyl)-pent-4-ynyloxy]-indol-1-yl}-acetic acid,

[rac]-2-{6-[5-(4-trifluoromethoxy-phenyl)-pent-4-ynyloxy]-indol-1-yl}-propionic acid, (6-{[3-(4-trifluoromethoxy-phenyl)-prop-2-ynylcarbamoyl]-methyl}-indol-1-yl)-acetic acid, (6-{[3-(4-trifluoromethyl-phenyl)-prop-2-ynylcarbamoyl]-methyl}-indol-1-yl)-acetic acid,
[6-({methyl-[5-(4-trifluoromethyl-phenyl)-pent-4-ynoyl]-amino}-methyl)-indol-1-yl]-acetic acid,
[6-({methyl-[3-(4-trifluoromethoxy-phenyl)-prop-2-ynyl]-carbamoyl}-methyl)-indol-1-yl]-acetic acid,
[rac]-{6-[1-methyl-5-(4-trifluoromethoxy-phenyl)-pent-4-ynyloxy]-indol-1-yl}-acetic acid, and pharmaceutically acceptable salts and/or esters thereof.

Particularly preferred compounds of formula I of the present invention are the following:
{6-[5-(4-trifluoromethoxy-phenyl)-pent-4-ynyloxy]-indol-1-yl}-acetic acid,
{6-[5-(4-trifluoromethyl-phenyl)-pent-4-ynyloxy]-indol-1-yl}-acetic acid,
{5-[5-(4-trifluoromethoxy-phenyl)-pent-4-ynyloxy]-indol-1-yl}-acetic acid,
{6-[5-(4-trifluoromethoxy-phenyl)-pent-4-ynylamino]-indol-1-yl}-acetic acid,
(6-{methyl-[5-(4-trifluoromethoxy-phenyl)-pent-4-ynoyl]-amino}-indol-1-yl)-acetic acid,
2-{6-[5-(4-trifluoromethoxy-phenyl)-pent-4-ynyloxy]-indol-1-yl}-propionic acid,
[rac]-{6-[1-methyl-5-(4-trifluoromethoxy-phenyl)-pent-4-ynyloxy]-indol-1-yl}-acetic acid, and pharmaceutically acceptable salts and/or esters thereof.

Especially preferred are also the following compounds of formula I of the present invention:
{6-[5-(4-trifluoromethoxy-phenyl)-pent-4-ynyloxy]-indol-1-yl}-acetic acid,
{6-[5-(4-trifluoromethyl-phenyl)-pent-4-ynyloxy]-indol-1-yl}-acetic acid, and pharmaceutically acceptable salts and/or esters thereof.

Furthermore, the pharmaceutically acceptable salts of the compounds of formula I and the pharmaceutically acceptable esters of the compounds of formula I individually constitute preferred embodiments of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula (I) as defined above, which process comprises reacting a compound of formula

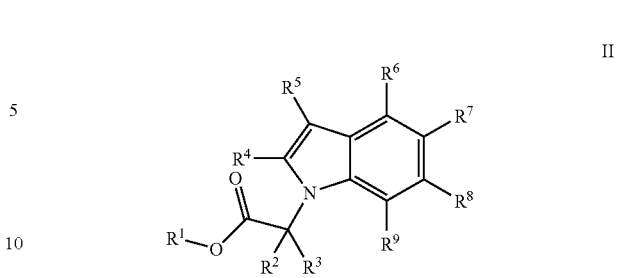

wherein $R^1$ is $C_{1-7}$-alkyl, $R^2$ to $R^9$ are as defined herein before and one of $R^6$, $R^7$, $R^8$ or $R^9$ is selected from —OH, —SH or —NHR$^{13}$, wherein $R^{13}$ is as defined herein before, with a compound of formula

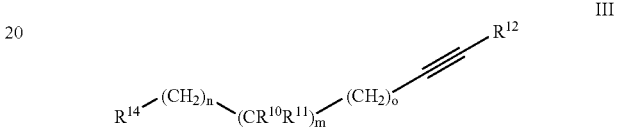

wherein $R^{10}$, $R^{11}$, $R^{12}$ n, m and o are as defined in claim 1 and $R^{14}$ is —OH, —Cl, —Br, —I or another leaving group, to obtain a compound of formula

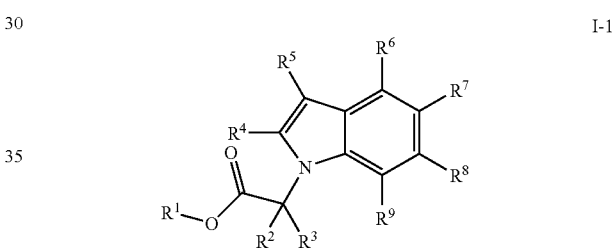

wherein one of $R^6$, $R^7$, $R^8$ and $R^9$ is

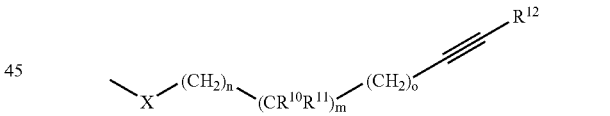

and wherein X is O, S, or —NR$^{13}$, $R^1$ is $C_{1-7}$-alkyl and X, $R^2$ to $R^{13}$ are as defined herein before, and optionally hydrolyzing the ester group to obtain a compound of formula I, wherein $R^1$ is hydroxen;

or, alternatively, reacting a compound of formula

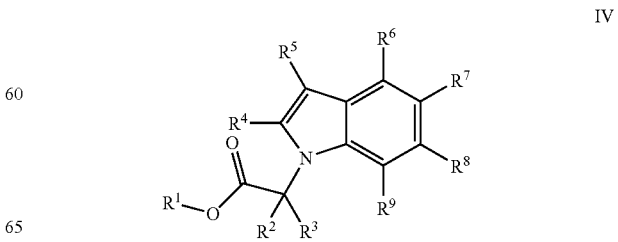

wherein $R^1$ is $C_{1-7}$-alkyl, $R^2$ to $R^9$ are as defined herein before and one of $R^6$, $R^7$, $R^8$ or $R^9$ is —$(CH_2)_p$—$NHR^{13}$, wherein $R^{13}$ and p are as defined herein before, with a compound of formula

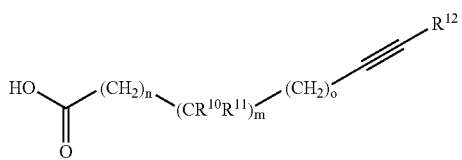

V wherein $R^{10}$, $R^{11}$, $R^{12}$, m, n and o are as defined herein before, to obtain a compound of formula

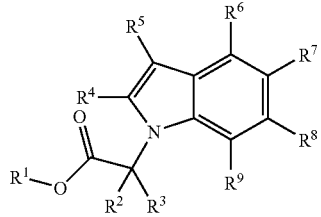

I-2 wherein one of $R^6$, $R^7$, $R^8$ and $R^9$ is

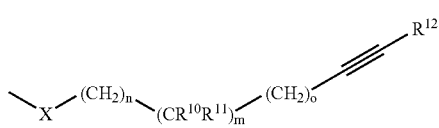

and wherein X is —$(CH_2)_p$—$NR^{13}CO$—, $R^1$ is $C_{1-7}$-alkyl and $R^2$ to $R^{13}$ and m, n, o and p are as defined herein before, and optionally hydrolyzing the ester group to obtain a compound of formula I, wherein $R^1$ is hydrogen;

or, alternatively, reacting a compound of formula

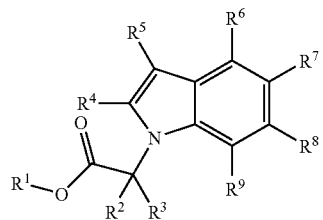

VI wherein $R^1$ is $C_{1-7}$-alkyl, $R^2$ to $R^9$ are as defined herein before and one of $R^6$, $R^7$, $R^8$ or $R^9$ is —$(CH_2)_p$—COOH, and p is defined as herein before, with a compound of formula

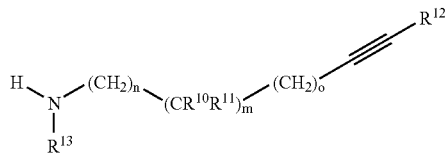

VII wherein $R^{10}$, $R^{11}$, $R^{12}$, $R^{13}$, m, n and o are as defined herein before, to obtain a compound of formula

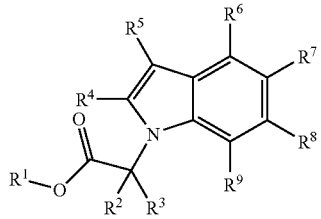

I-3 wherein one of $R^6$, $R^7$, $R^8$ and $R^9$ is

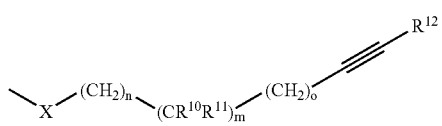

and wherein X is —$(CH_2)_p$—$CONR^{13}$, $R^1$ is $C_{1-7}$-alkyl and $R^2$ to $R^{13}$ and m, n, o and p are as defined herein before, and optionally hydrolyzing the ester group to obtain a compound of formula I, wherein $R^1$ is hydrogen;

or, alternatively, reacting a compound of formula

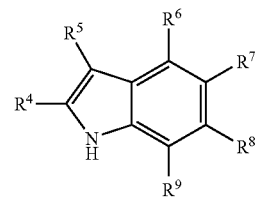

VIII wherein $R^4$ to $R^9$ are as defined herein before, with a compound of formula

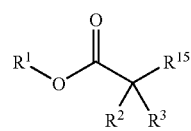

IX wherein $R^1$ is $C_{1-7}$-alkyl, $R^2$ and $R^3$ are as defined herein before and $R^{15}$ is halogen, triflate or another leaving group, to obtain a compound of formula

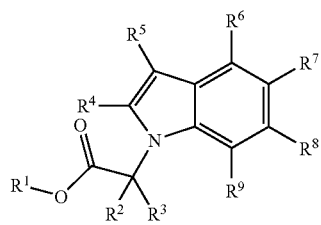

I wherein $R^1$ is $C_{1-7}$-alkyl and $R^2$ to $R^9$ are as defined herein before, and optionally hydrolyzing the ester group to obtain a compound of formula I, wherein $R^1$ is hydrogen.

As described above, the compounds of formula (I) of the present invention can be used as medicaments for the treatment and/or prevention of diseases which are modulated by PPARδ and/or PPARα agonists. Examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), elevated blood pressure, endothelial dysfunction, procoagulant state, dyslipidemia, polycystic ovary syndrome, inflammatory diseases (such as e.g. Crohn's disease, inflammatory bowel disease, colitis, pancreatitis, cholestasis/fibrosis of the liver, rheumatoid arthritis, osteoarthritis, psoriasis and other skin disorders, and diseases that have an inflammatory component such as e.g. Alzheimer's disease or impaired/improvable cognitive function) and proliferative diseases (cancers such as e.g. liposarcoma, colon cancer, prostate cancer, pancreatic cancer and breast cancer). The use as medicament for the treatment of low HDL cholesterol levels, high LDL cholesterol levels, high triglyceride levels, and the metabolic syndrome (syndrome X) is preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are modulated by PPARδ and/or PPARα agonists. Examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases.

In another embodiment, the invention relates to a method for the treatment and/or prevention of diseases which are modulated by PPARδ and/or PPARα agonists, which method comprises administering a compound of formula (I) to a human or animal. Preferred examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases.

The invention further relates to the use of compounds as defined above for the treatment and/or prevention of diseases which are modulated by PPARδ and/or PPARα agonists. Preferred examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases.

In addition, the invention relates to the use of compounds as defined above for the preparation of medicaments for the treatment and/or prevention of diseases which are modulated by PPARδ and/or PPARα agonists. Preferred examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases. Such medicaments comprise a compound as defined above.

The compounds of formula (I) can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

The synthesis of compounds with the general structure I of the present invention, particularly compounds according to formula Ia (scheme 1) with X equal to oxygen can be accomplished according to scheme 1.

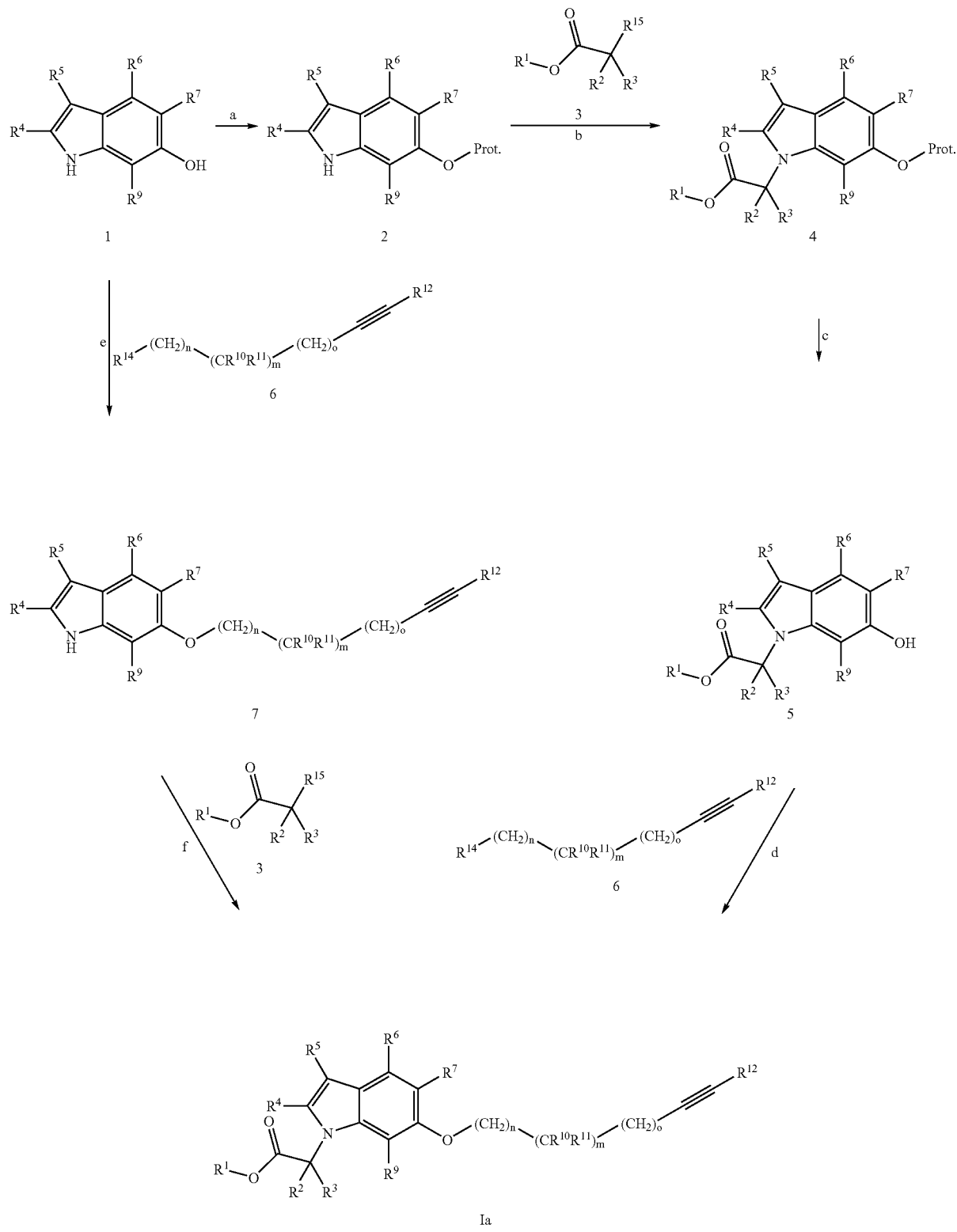
Scheme 1

6-Hydroxyindoles 1 and the regioisomeric 4-, 5- and 7-hydroxyindoles are commercially available, known or can be synthesized by methods known in the art. The hydroxy function of compounds 1 can be protected by methods described in the literature, e.g. by treating them with tert-butyldimethylsilyl chloride in the presence of imidazole, preferably at room temperature in solvents like N,N-dimethylformamide, to obtain the corresponding tert-butyldimethylsilyl ethers 2 (step a). N-Alkylation of intermediates 2 with carboxylic acid esters 3, where $R^{15}$ can be equal to e.g. chlorine, bromine, triflate, or another leaving group, delivers indoles 4 and can be performed by standard technology; e.g. in the presence of $K_2CO_3$ or $Cs_2CO_3$ at temperatures between 10° C. and the reflux temperature of the solvent in a solvent like acetonitrile or acetone or in the presence of sodium hydride at temperatures between −10° C. and 50° C. in a solvent like N,N-dimethylformamide (step b). Ester derivatives 3 are commercially available or can be synthesized by methods known in the art. Deprotection of indoles 4 by methods described in the literature, e.g. by treatment with tetrabutyl ammonium fluoride at temperatures between −15° C. and ambient temperature in a solvent like tetrahydrofuran, provided that the protection group is a silyl ether, gives hydroxyindoles 5 (step c). Alkyne compounds 6 (prepared as outlined in schemes 5 to 7) are condensed with hydroxyindoles 5 according to well known procedures: if $R^{14}$ represents a hydroxy group e.g. via Mitsunobu-reaction, with triphenylphosphine and di-tert-butyl-, diisopropyl- or diethyl-azodicarboxylate as reagents, or by using tributylphosphine and N,N,N',N'-tetramethyl azodicarboxamide; this transformation is preferably carried out in a solvent like toluene, dichloromethane or tetrahydrofuran at ambient temperature. Alternatively, if $R^{14}$ represents a halide, mesylate or tosylate moiety, alkyne compounds 6 can be reacted with hydroxyindoles 5 in solvents like N,N-dimethylformamide, acetonitrile, acetone or methyl-ethyl ketone in the presence of a base like cesium or potassium carbonate in a temperature ranging from room temperature to 140° C., preferably around 50° C., to yield ether compounds Ia (step d). Alkynes 6 with $R^{14}$=OH can also be transformed in situ to the corresponding triflates by treatment with trifluoromethanesulfonic anhydride/2,6-di-tert-butylpyridine in dichloromethane at 0° C. to room temperature. The triflates are then reacted with hydroxyindoles 5 in solvents like N,N-dimethylformamide, dimethylsulfoxide, acetonitrile, acetone or methyl-ethyl ketone in the presence of a base like cesium or potassium carbonate at a temperature ranging from room temperature to 140° C., preferably around 50° C. to yield ether compounds Ia (step d). Carboxylic acid esters Ia can alternatively be synthesized via regioselective condensation of alkynes 6 with hydroxyindoles 1 under the conditions given in step d (step e) and subsequent N-alkylation of the obtained ethers 7 with alkylating reagents 3 as described for the synthesis of esters 4 in step b (step f). In addition, indoles 7 or esters Ia with $R^{12}$ equal to hydrogen can be subjected to Sonogashira coupling conditions (e.g. see descriptions in schemes 5 and 6 or Natchus, Michael G.; Bookland, Roger G.; Laufersweiler, Matthew J.; Pikul, Staszek; Almstead, Neil G.; De, Biswanath; Janusz, Michael J.; Hsieh, Lily C.; Gu, Fei; Pokross, Matthew E.; Patel, Vikram S.; Garver, Susan M.; Peng, Sean X.; Branch, Todd M.; King, Selane L.; Baker, Timothy R.; Foltz, David J.; Mieling, Glen E. Journal of Medicinal Chemistry (2001), 44(7), 1060-1071) to give alkynes 7 with $R^{12}$≠H or the final compounds Ia, respectively. Esters of formula Ia can optionally be hydrolyzed according to standard procedures, e.g. by treatment with an alkali hydroxide like LiOH or NaOH in a polar solvent mixture like tetrahydrofuran/ethanol/water leading to carboxylic acids Ia. If the alkyne compounds 6 (prepared as described in schemes 5 to 7) and/or the hydroxyindoles 5 contain chiral centers, ester compounds Ia and carboxylic acids Ia can be obtained as mixtures of diastereomers or enantiomers, which can be separated by methods well known in the art, e.g. (chiral) HPLC or crystallization.

An analogous reaction scheme with the same reaction sequences applies for the isomeric compound series leading to compounds of general formula I, particularly compounds according to formula Ib:

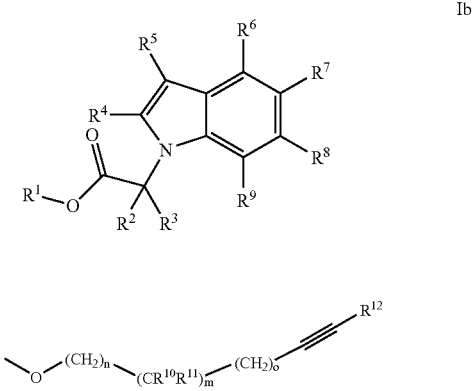

The synthesis of compounds with the general structure I, particularly compounds with X equal to S can be accomplished in close analogy to the synthesis of the corresponding analogues with X equal to oxygen. Suitable sulfur containing intermediates are known, can be prepared by methods known in the art (compare e.g. M. Matsumoto, N. Watanabe, *Heterocycles* 1987, 26, 913-916 or E. Piers, V. B. Haarstadt, R. J. Cushley, R. K. Brown, *Canadian Journal of Chemistry* 1962, 40, 511-517) or can be prepared from suitable intermediates carrying an aromatic hydroxy function. In such intermediates, optionally carrying one or more protective functions, the aromatic OH group can be replaced by the corresponding aromatic SH function by methods known in the art. For example by a three step sequence as described in J. Labeled Compounds & Radiopharmaceuticals 43(7), 683-691, (2000): i) transformation of the aromatic hydroxy moiety into its trifluoromethanesulfonate (triflic anhydride, triethylamine, dichloromethane, at low temperature, preferably around −30° C.); ii) treatment of the triflate with triisopropylsilanethiolate, tetrakis(triphenylphosphine)-palladium(0) in solvent mixtures like toluene and tetrahydrofuran in a temperature range between 60° C. and 150° C.; iii) treatment of the silyl sulfide with hydrogen chloride in methanol preferably around 0° C. to liberate the aromatic SH moiety.

The synthesis of compounds with the general structure I, particularly compounds according to formula Ic, with X equal to nitrogen, can be accomplished according to scheme 2.

Scheme 2

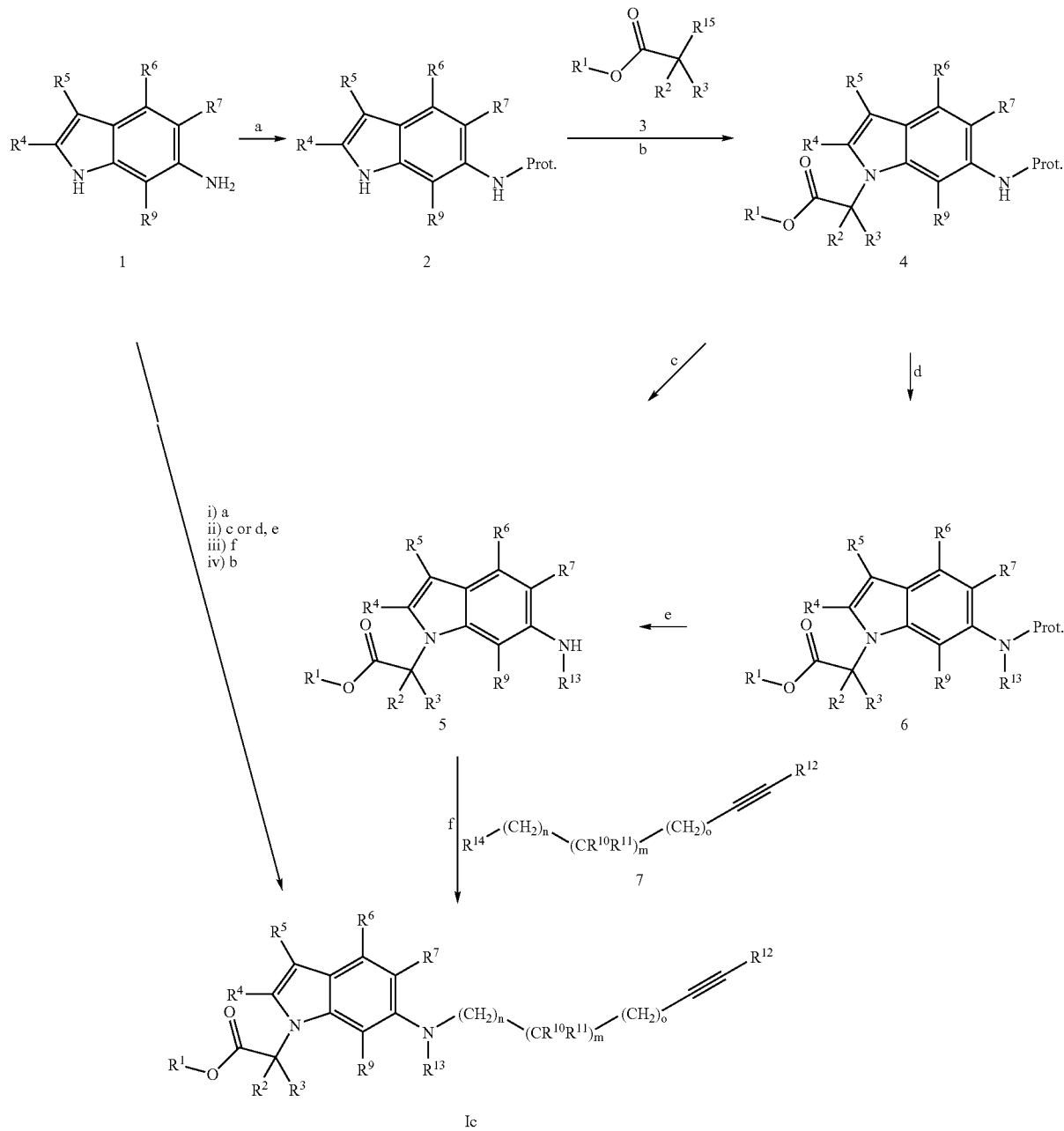

6-Aminoindoles 1 and the regioisomeric 4-, 5- and 7-aminoindoles are commercially available, known or can be synthesized by methods known in the art, e.g. starting from the analogous hydroxyindoles. In such intermediates, optionally carrying one or more protective functions, the aromatic hydroxy group can be replaced by an amino function, e.g. by applying the following three step sequence described in Tetrahedron Letters 43(42), 7617-7619(2002): i) transformation of the hydroxyindole moiety into its trifluoro-methanesulfonate (triflic anhydride, 2,6-lutidine, 4-dimethylaminopyridine, dichloromethane, 0° C. to room temperature; ii) treatment of the triflate with benzophenone imine, di-palladium-tris(dibenzylideneacetone) complex, S-(−)-2,2'-bis (diphenylphosphino)-1,1'-binaphthyl, cesium carbonate, toluene, in a Schlenk tube at temperatures around 120° C.; iii) treatment with catalytic amounts of hydrochloric acid in wet tetrahydrofuran preferably at room temperature to liberate the aromatic $NH_2$ moiety. This amino function of compounds 1 can be protected by methods described in the literature, e.g. by treatment with di-tert-butyl dicarbonate optionally in the presence of a base like e.g. triethylamine, preferably at ambient temperature in solvents like methanol, tetrahydrofuran or dichloromethane, to yield indoles 2 (step a). Alkylation of intermediates 2 at the nitrogen in position 1 with carboxylic acid ester 3, where $R^{15}$ can be equal to e.g. chlorine, bromine, triflate or another leaving group, delivers indoles 4 and can be performed by standard technology; e.g. in the presence of $K_2CO_3$ or $Cs_2CO_3$ at temperatures between 10° C. and the reflux temperature of the solvent in a solvent like acetonitrile, acetone or N,N-dimethylformamide (step b). Removal of the protecting group under standard conditions, e.g. by using hydrochloric acid in ethyl acetate, preferably at temperatures between 0° C. and ambient temperature, affords amines 5 with $R^{13}$ being equal to hydrogen (step c). Intermediates 4 can optionally be alkylated at the nitrogen in 6-position using sodium hydride and a reactive alkyl halogenide/mesylate or triflate to give compounds 6 (step d) which can be deprotected as described in step c to obtain amines 5 with $R^{13} \neq $ hydrogen (step e). Reaction of aminoindoles 5 with alkynes 7 (prepared as outlined in schemes 5 to 7) using sodium hydride or sodium, potassium or cesium carbonate in N,N-dimethylformamide, dimethylsulfoxide, dimethylacetamide or tetrahydrofuran, at a temperature ranging from 0° C. to 140° C., preferably at ambient temperature, leads to compounds Ic (step f). Alternatively, alkynes 7 with $R^{14}$=OH can be transformed in situ to the corresponding triflates by treatment with trifluoromethane-sulfonic anhydride/2,6-di-tert-butylpyridine in dichloromethane at 0° C. These triflates are then reacted with amines 5 in the presence of a base such as sodium hydride in solvents like nitromethane at temperatures between ambient temperature and 60° C. to yield compounds Ic [following a procedure from Belostotskii, Anatoly M., Hassner, A., Tetrahedron Lett. 1994, 35(28), 5075-6] (step f). Further, steps d and f can be exchanged to synthesize compounds Ic with $R^{13} \neq $ hydrogen and steps f and c can be exchanged in order to synthesize compounds Ic with $R^{13}$ being equal to hydrogen. In addition, secondary amines Ic ($R^{13}$=H) can be reductively methylated with an aqueous solution of $NaH_2PO_3$ and formaldehyde at temperatures between ambient temperature and 65° C. [Loibner, H., Pruckner, A., Stuetz, A., Tetrahedron Lett. 1984, 25, 2535-2536] to give compounds Ic with $R^{13}$=Me. Alternatively, esters Ic with $R^{12}$ equal to hydrogen can be subjected to Sonogashira coupling conditions (e.g. see descriptions in schemes 5 and 6 or Natchus, Michael G.; Bookland, Roger G.; Laufersweiler, Matthew J.; Pikul, Staszek; Almstead, Neil G.; De, Biswanath; Janusz, Michael J.; Hsieh, Lily C.; Gu, Fei; Pokross, Matthew E.; Patel, Vikram S.; Garver, Susan M.; Peng, Sean X.; Branch, Todd M.; King, Selane L.; Baker, Timothy R.; Foltz, David J.; Mieling, Glen E. Journal of Medicinal Chemistry (2001), 44(7), 1060-1071) to give the final compounds Ic. Esters Ic can further be synthesized starting from aminoindoles 1—optionally using one or more protecting groups—applying the following reaction sequence: i) protection of the amino group as described in step a; ii) protecting group manipulations and introduction of $R^{13}$ as described in steps c, d and e; iii) reaction with building blocks 7 as described in step f (if $R^{13}$ is equal to hydrogen steps i) and ii) can be left out); iv) alkylation at the indole 1N-atom with carboxylic acid esters 3 as described in step b. Esters of formula Ic can optionally be hydrolyzed according to standard procedures, e.g. by treatment with an alkali hydroxide like LiOH or NaOH in a polar solvent mixture like tetrahydrofuran/ethanol/water leading to carboxylic acids Ic. If alkyne compounds 7 (prepared as described in schemes 5 to 7) and/or aminoindoles 5 contain chiral centers, ester compounds Ic and carboxylic acids Ic can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization with optically pure amines such as e.g. (R) or (S)-1-phenyl-ethylamine, (R) or (S)-1-naphthalen-1-yl-ethylamine, brucine, quinine or quinidine or by separation of the antipodes by specific chromatographic methods using either a chiral adsorbens or a chiral eluent.

An analogous reaction scheme with the same reaction sequences applies for the isomeric compound series leading to compounds of general formula I, particularly compounds according to formula Id:

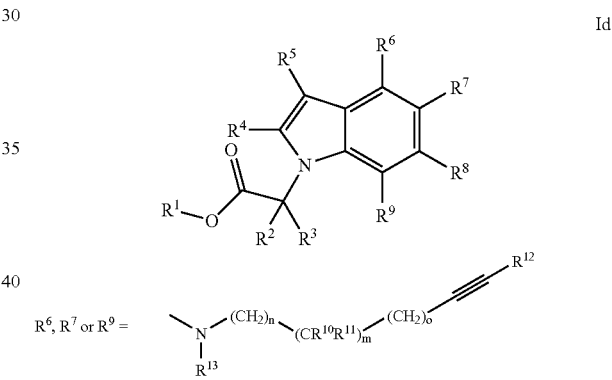

The synthesis of compounds with the general structure I, particularly compounds according to formula Ie and If, with X equal to $(CH_2)_p NR^{13} CO$, or $(CH_2)_p CONR^{13}$ can be accomplished according to scheme 3.

Scheme 3

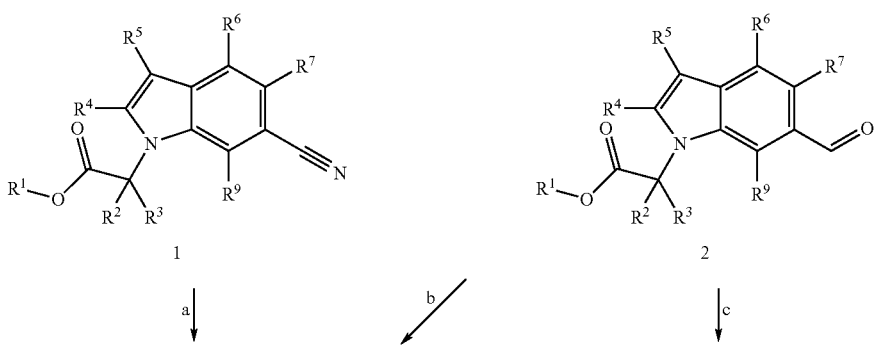

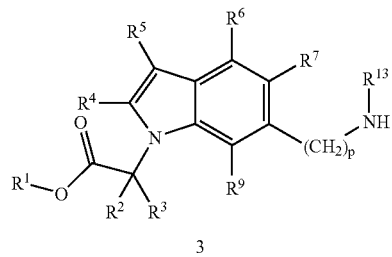

3

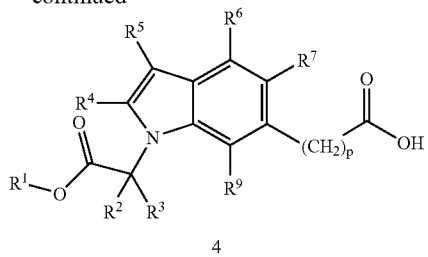

4

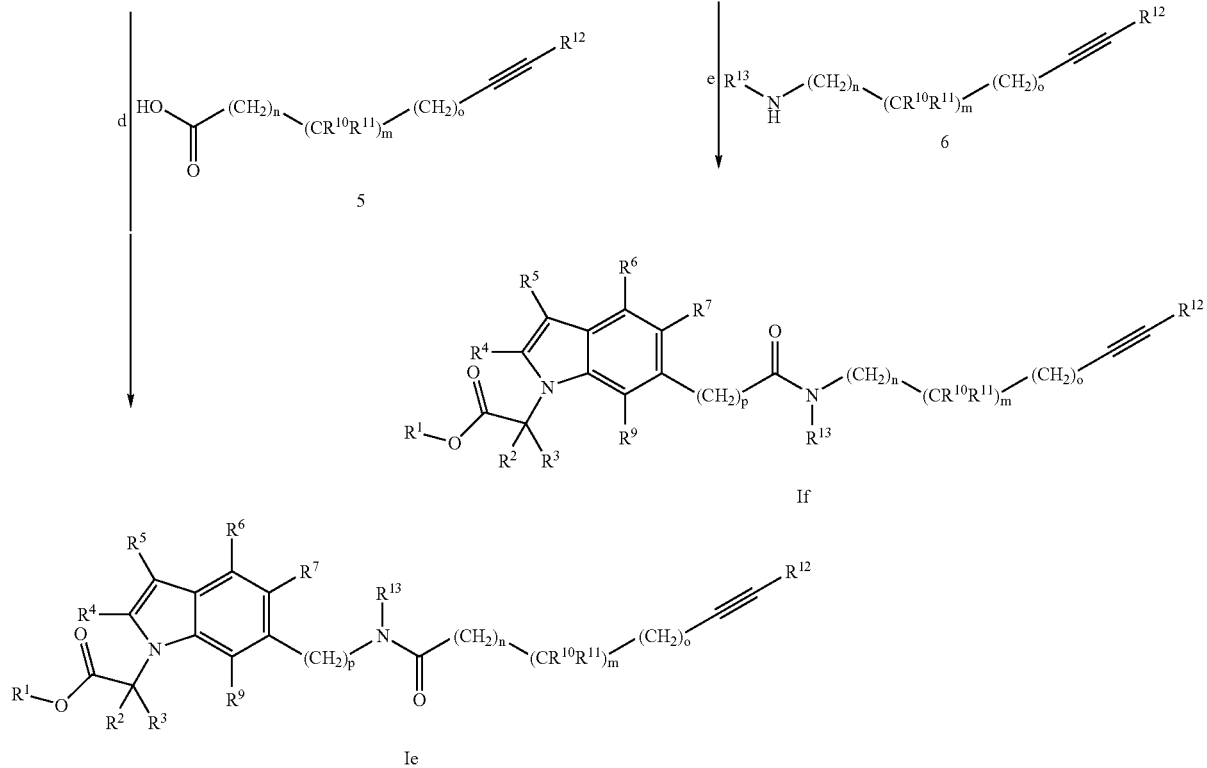

Nitriles 1 and aldehydes 2 can be prepared from the corresponding cyano- or formyl-indoles (which are known, commercially available or can be prepared by methods known in the art) by reaction with esters having a leaving group in the alpha position (compounds 3 in schemes 1 and 2) in the presence of a base like potassium or cesium carbonate in solvents like acetone, methyl-ethyl ketone, acetonitrile or N,N-dimethylformamide in a temperature range between room temperature and 140° C. Hydrogenation of nitrile compounds 1, e.g. using catalytic amounts of platinum dioxide in a mixture of ethanol and chloroform, leads to compounds 3 with p=1 (step a). The preparation of compounds 3 with p=0 has been described in scheme 2 (compounds 5, scheme 2). Compounds 3 with p=2 can be prepared from compounds 2 in a two step procedure: i) treatment with nitro-methane and ammonium acetate at a temperature around 110° C. to form the corresponding nitro styrene compounds; ii) reduction to the aminoethyl-substituted indoles by methods known in the art (step b). In order to introduce substituents $R^{13} \neq H$, e.g. BOC-protection of compounds 3, followed by alkylation and subsequent removal of the BOC group can be performed similarly as described in scheme 2.

Compounds 4 with p=0 can be prepared by oxidizing aldehydes 2 under standard conditions to aromatic acids 4 (e.g. with sodium chlorite, sodium dihydrogen-phosphate in a mixture of tert-butanol and water and in the presence of 3-methyl-2-butene at temperatures around room temperature) (step c). Alternatively, acids 4 with p=0 can be synthesized from 1H-indole-7-carboxylic acid derivatives (which are known, commercially available or can be prepared by methods known in the art) by reacting them with esters having a leaving group in the alpha position (compounds 3 in schemes 1 and 2)—optionally using one or more protecting groups—in the presence of a base like potassium or cesium carbonate in solvents like acetone, methyl-ethyl ketone, acetonitrile or N,N-dimethylformamide in a temperature range between room temperature and 140° C. Compounds 4 with p=1 can be prepared from compounds 2 by a Wittig reaction using (methoxymethyl)-triphenylphosphonium chloride as reagent, transformation of the resulting enol ethers to the corresponding aldehydes and subsequent oxidation to the acids 4 (step c). Compounds 4 with p=2 can be prepared from compounds 2 e.g. by a Horner-Wadsworth-Emmons reaction using dimethyl(benzyloxy-carbonyl)methyl phosphonate, followed by selective reduction of the double bond and cleavage of the ester function applying methods well known in the art (step c). Condensation of amines 3 or acids 4 with acids 5 or amines 6 (prepared as outlined in schemes 5 to 7) can be performed applying standard literature procedures for amide formation, such as the use of N-(3-dimethylaminopropyl)-N'-ethyl-carbodiimide-hydrochloride and 4-dimethylamino-pyridine in dichloromethane at temperatures between 0° C. and room temperature yielding compounds Ie (step d) or If (step e). Alternatively, amines 3 or acids 4 can be condensed with alkynes 5 or 6 with $R^{12}$=H (prepared as outlined in schemes 5 to 7) to give alkynes Ie ($R^{12}$=H) (step d) or If ($R^{12}$=H) (step e). Intermediates Ie ($R^{12}$=H) or If ($R^{12}$=H) can further be processed via Sonogashira coupling as described in schemes 5 and 6 to the final compounds Ie or If [e.g. see description in schemes 5 and 6 or Natchus, Michael G.; Bookland, Roger G.; Laufersweiler, Matthew J.; Pikul, Staszek; Almstead, Neil G.; De, Biswanath; Janusz, Michael J.; Hsieh, Lily C.; Gu, Fei; Pokross, Matthew E.; Patel, Vikram S.; Garver, Susan M.; Peng, Sean X.; Branch, Todd M.; King, Selane L.; Baker, Timothy R.; Foltz, David J.; Mieling, Glen E. Journal of Medicinal Chemistry (2001), 44(7), 1060-1071]. Esters Ie and If can alternatively be synthesized starting from cyano-1H-indoles instead of starting from nitriles 1 or starting from formyl-1H-indoles instead of starting from aldehydes 2 applying the synthetic routes described in scheme 3, optionally using protecting groups (compare e.g. U.S. Pat. No. 4,378,368; cyano- and formyl-indoles are known, commercially available or can be prepared by methods known in the art). Using this synthetic strategy, the reaction with esters having a leaving group in the alpha position (compounds 3 in schemes 1 and 2) in the presence of a base like potassium or cesium carbonate in solvents like acetone, methyl-ethyl ketone, acetonitrile or N,N-dimethylformamide in a temperature range between room temperature and 140° C. is carried out after the amide bond formation steps d or e, to obtain the final compounds Ie or If, respectively. Esters of formula Ie or If can optionally be hydrolyzed according to standard procedures, e.g. by treatment with an alkali hydroxide like LiOH or NaOH in a polar solvent mixture like tetrahydrofuran/ethanol/water, giving carboxylic acids Ie or If. If the alkyne compounds 5 and 6 (prepared as described in schemes 5 to 7) and/or the indoles 3 and 4 contain chiral centers, ester compounds Ie and If and carboxylic acids Ie and If can be obtained as mixtures of diastereomers or enantiomers, which can be separated by methods well known in the art, e.g. (chiral) HPLC or crystallization.

An analogous reaction scheme with the same reaction sequences applies for the isomeric compound series leading to compounds of general formula I, particularly compounds according to formula Ig and Ih:

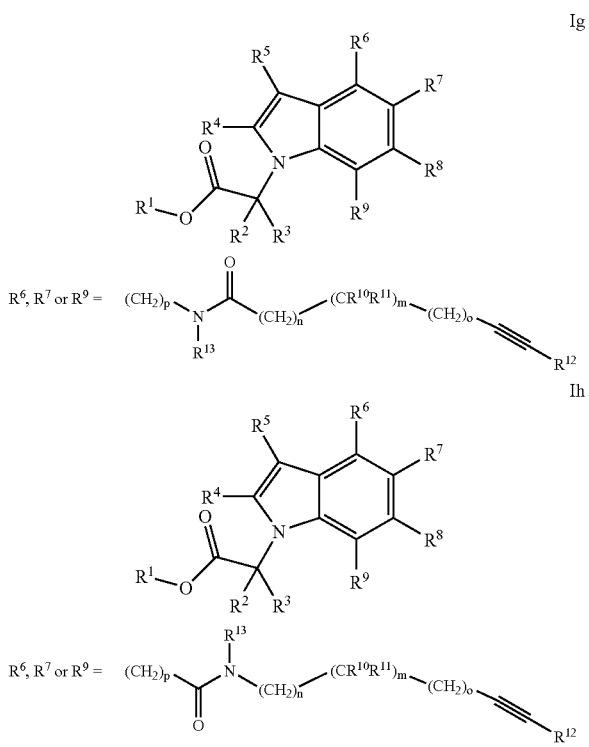

6-Hydroxyindoles 1 (scheme 1) and O-protected 6-hydroxyindoles 2 (scheme 1) as well as their regioisomeric 4-, 5- and 7-hydroxyindole analogues are known or can be synthesized by methods known in the art. Examples for possible syntheses of these key intermediates (compounds 6 and 7 in scheme 4) are given in scheme 4 for $R^8$ in I being equal to hydroxy or protected hydroxy. Analogous key intermediates where $R^6$, $R^7$ or $R^9$ is equal to hydroxy or hydroxy carrying a protecting group can be synthesized applying the same reaction sequence.

Scheme 4

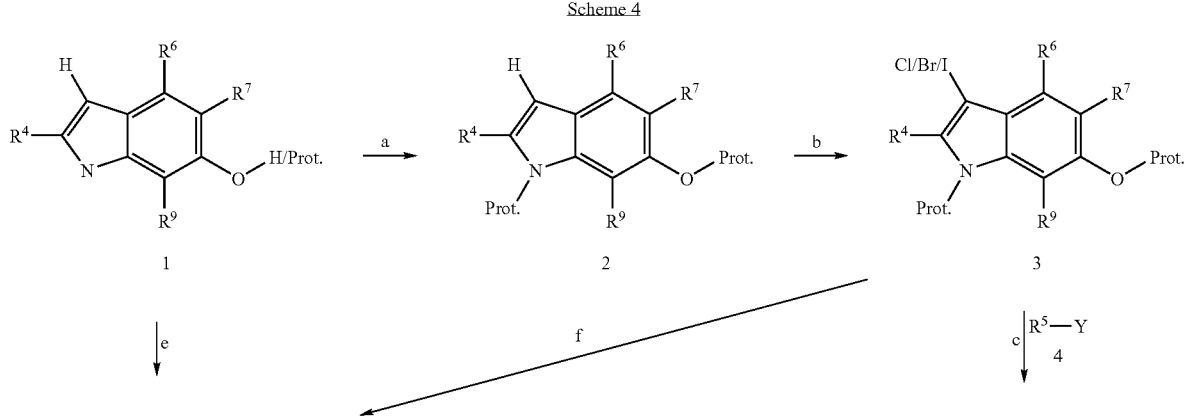

-continued

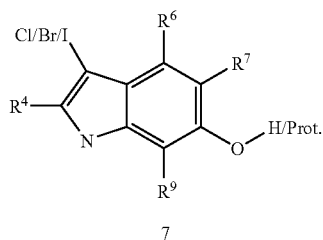
7

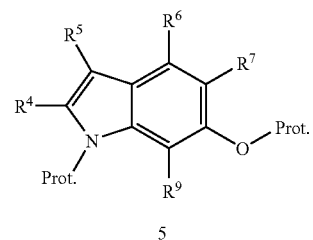
5

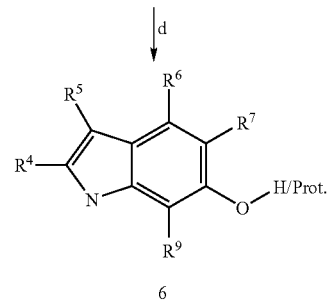
6

Introduction of a protecting group at the nitrogen atom of indoles 1 can be performed under standard conditions, e.g. by deprotonation with a base like n-butyllithium, preferably at −78° C., and subsequent addition of e.g. tert-butyldimethylsilyl chloride at temperatures between −78° C. and ambient temperature in solvents like tetrahydrofuran (step a). Halogenation of protected indoles 2, e.g. through reaction with N-halosuccinimides at temperatures between −78° C. and ambient temperature in solvents like tetrahydrofuran delivers 3-halo indoles 3 (step b). Compounds 3 can—following halogen metal exchange, preferably with tert-butyllithium at −78° C. in solvents like tetrahydrofuran—be reacted with alkylating reagents 4 with Y e.g. being a chlorine, bromine or iodine atom, preferably with alkyl iodides, at temperatures between −78° C. and ambient temperature in solvents like tetrahydrofuran, to form indoles 5 bearing a substituent in position 3 (step c). N-Deprotection or simultaneous N- and O-deprotection of compounds 5 leading to building blocks 6 can be performed by methods described in the literature, e.g. by treatment with tetrabutyl ammonium fluoride at temperatures between −15° C. and ambient temperature in a solvent like tetrahydrofuran, provided that the protecting groups are silyl ethers and/or silylated indoles (step d).

Building blocks 7 carrying a chlorine, bromine or iodine substituent in position 3 can be synthesized by halogenation of indoles 1, optionally carrying a protecting group at the hydroxy function, e.g. by reaction with N-chlorosuccinimide at temperatures between −15° C. and the reflux temperature of the solvent in solvents like dichloromethane or chloroform (step e). Alternatively, the same halo-indoles 7 can be obtained via N-deprotection or N- and O-deprotection of indoles 3 as described in step d (step f).

Using appropriate protecting groups, the synthesis of hydroxyindole derivatives 6 and 7 described in scheme 4 can be transferred to the synthesis of the corresponding 4-, 5-, 6- or 7-thioindole or 4-, 5-, 6-, or 7- aminoindole analogues, respectively.

Schemes 5 to 7 describe the synthesis of alkyne building blocks 6 (scheme 1), identical to compounds 7 (scheme 2), and acid-5 and amine-building blocks 6 (scheme 3).

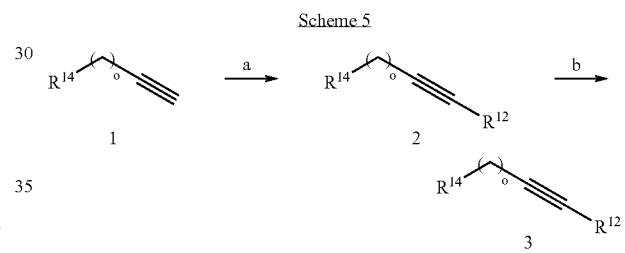

Hydroxy alkynes 1 ($R^{14}$=OH) or amino alkynes 1 ($R^{14}$=$NHR^{13}$ or N-protected $NR^{13}$) or alkyne esters 1 ($R^{14}$=COOalkyl) are known or can be prepared by methods known in the art. Alkynes 1 undergo palladium- and copper mediated coupling reactions with halo aryls or halo heteroaryls to give alkynes 2 (step a) wherein $R^{12}$ is aryl or heteroaryl. These Sonogashira couplings are preferably performed using catalytic amounts of $Pd(PPh_3)_4$/CuI at 45° C. to 80° C. in piperidine, in analogy to a literature procedure [Stara, Irena G.; Stary, Ivo; Kollarovic, Adrian; Teply, Filip; Saman, David; Fiedler, Pavel. Collect. Czech. Chem. Commun. (1999), 64(4), 649-672], $Pd(PPh_3)_4$/CuI/$Et_3$N at room temperature in DMF [Natchus, Michael G.; Bookland, Roger G.; Laufersweiler, Matthew J.; Pikul, Staszek; Almstead, Neil G.; De, Biswanath; Janusz, Michael J.; Hsieh, Lily C.; Gu, Fei; Pokross, Matthew E.; Patel, Vikram S.; Garver, Susan M.; Peng, Sean X.; Branch, Todd M.; King, Selane L.; Baker, Timothy R.; Foltz, David J.; Mieling, Glen E. Journal of Medicinal Chemistry (2001), 44(7), 1060-1071] or $Pd(PPh_3)_2Cl_2$/CuI/$Et_3$N at room temperature in acetonitrile or THF [Thorand, Stephan; Krause, Norbert Journal of Organic Chemistry (1998), 63(23), 8551-8553] (step a). Finally, alcohols 2 ($R^{14}$=OH) of scheme 5 can be converted into compounds of formula 3 ($R^{14}$=OMesylate, Op-Tosylate, Halide or Triflate), e.g. by treatment with methanesulfonyl chloride or p-toluenesulfonyl chloride in dichloromethane in the presence of a base like triethylamine preferably in a temperature range between −20° C. and room temperature or by treatment with thionyl chloride in dichloromethane at 0° C. to room temperature or by reaction with carbon tetrachloride or carbon tetrabromide and triphenylphosphine in solvents like tetrahydrofuran, preferably in a temperature range between room temperature and the reflux temperature of the solvents or by treatment with triflic anhydride, 2,6-lutidine and 4-dimethylaminopyridine in dichloromethane between −30° C. and room temperature; thus yielding compounds of formula 3 as methane-sulfonates, p-toluene sulfonates, chlorides, bromides or triflates, respectively (step b). Deprotection of esters 2 ($R^{14}$=COOalkyl) or amines 2 ($R^{14}$=N-protected $NR^{13}$) yields acids 3 (R14=COOH) or amines 3 ($R^{14}$=$NHR^{13}$) and can be accomplished using procedures well known in the art (step b). All reactions described in scheme 5 are compatible with terminal alkynes, therefore in scheme 5 $R^{12}$ can also be a hydrogen atom.

building block 5 used in scheme 3). Compounds 3 can be chiral and can optionally be separated into optically pure antipodes by methods well known in the art, e.g. by chromatography on a chiral HPLC column, or if $R^{16}$ is equal to hydrogen by derivatization with an optically pure alcohol to form esters, which can be separated by conventional HPLC chromatography and then converted back to the enantiomerically pure acid. In addition, compounds 1 can be converted into chiral amides which can be used for asymmetric alkylation reactions being well known to a person skilled in the art. Esters 3 can be reduced with lithiumaluminium hydride at temperatures ranging from −78° C. to 0° C., preferable at −20° C. in solvents like THF to give alcohols 4 ($R^{10'}$=$R^{11'}$=H) (step c). Esters 3 ($R^{16}$≠H) can further be converted into tertiary alcohols 4 with $R^{10'}$=$R^{11'}$ through reaction with alkyl organometallic reagents, preferably using Scheme 6

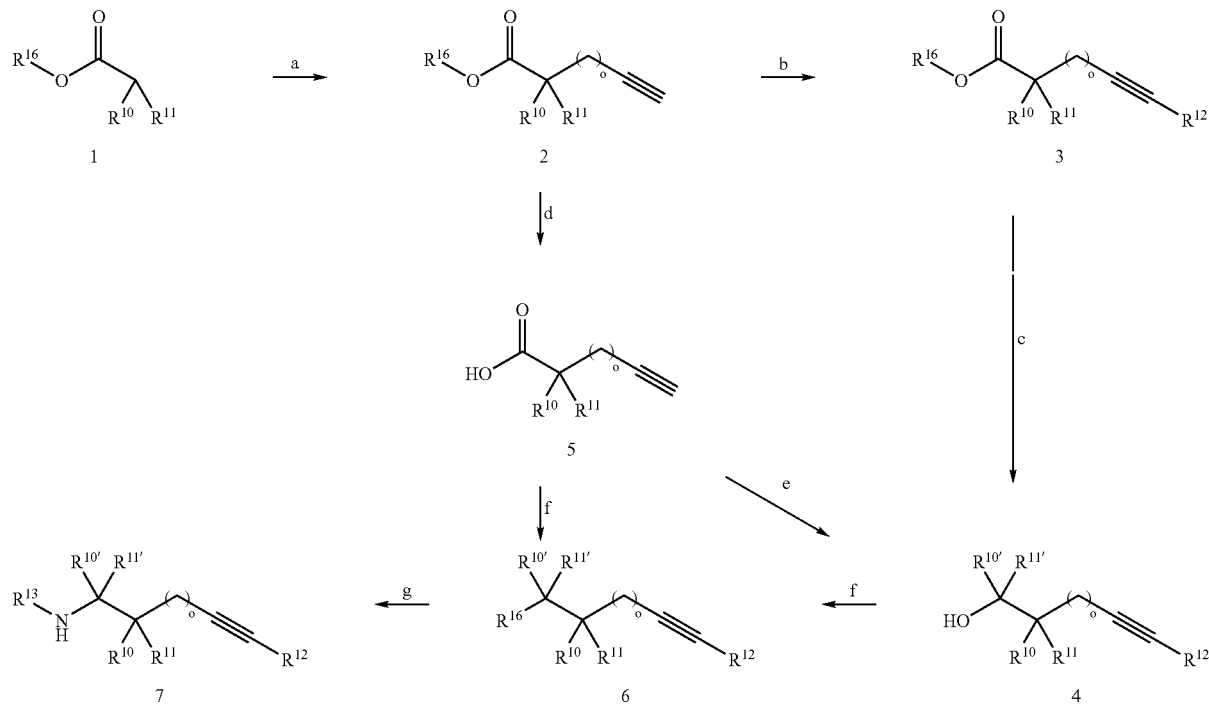

Alpha mono- or di-substituted esters 2 ($R^{10}$ and/or $R^{11}$≠H) can be synthesized via treatment of esters 1 ($R^{16}$≠H) with a base like LDA or HMDS in solvents like tetrahydrofuran or 1,2-dimethoxyethane, followed by addition of one or sequentially two different alkyl halides and one alkyne halide (o>0)-optionally carrying a protecting group—at temperatures between −78° C. and room temperature, optionally using DMPU or HMPA as cosolvents (step a). To synthesize alkynes 2 with o being 0,3-butynoic acid derivatives—optionally carrying a protecting group—can be alkylated at the alpha carbon atom with $R^{10}$- and/or $R^{11}$-alkyl halides by methods known in the art. Deprotection if necessary, applying methods known to a person skilled in the art, and Sonogashira coupling as described in step a of scheme 5 provides alkynes 3 (step b). Alternatively, compounds 3 can be synthesized by reacting enolates of compounds 1 with compounds 3 of scheme 5 with $R^{14}$ being a leaving group, e.g. a halide. Hydrolysis of esters 3 gives access to acids 3 ($R^{16}$=H; acid alkyl Grignard compounds in a solvent like tetrahydrofuran or ether, preferably between −15° C. and the reflux temperature of the solvent (step c); $R^{10'}$ and $R^{11'}$ represent substituents as defined herein before for $R^{10}$ and $R^{11}$. Alcohols 4 with $R^{10'}$ not equal to $R^{11'}$ can be prepared by a sequential procedure: i) saponification of esters 3 to the corresponding acids; ii) treatment with $R^{10'}$Li, optionally in the presence of a Cu(I) salt, in ether or tetrahydrofuran to yield alkyl ketones —$COR^{10'}$; iii) subsequent reaction with $R^{11'}$Li or lithium aluminium hydride in ether or tetrahydrofuran (step c). In addition, esters 3 can be converted to secondary alcohols 4 ($R^{10'}$≠H; $R^{11'}$=H) by a two step procedure: i) reduction to the corresponding aldehydes by methods known in the art, e.g. by treatment with diisobutylaluminium hydride at temperatures preferably around −70° C.; ii) conversion of the aldehydes to the corresponding secondary alcohols 4 through reaction with alkyl organometallic compounds, preferably under the conditions given for the transformation of esters 3 to tertiary alcohols 4 described above (step c); this step can optionally be carried out in enantioselective or diastereoselective fashion using methods well known to a person skilled in the art. Alternatively, alkynes 2 can first be reduced with lithiumaluminium hydride to form alcohols 5 (step d), which undergo Sonogashira coupling reactions as described in step a of scheme 5 to yield building blocks 4 (step e). Alcohols 4 and 5 can be converted to the activated building blocks of formula 6 ($R^{16}$=OMesylate, Op-Tosylate, Halide or Triflate), e.g. by treatment with methanesulfonyl chloride or p-toluenesulfonyl chloride in dichloromethane in the presence of a base like triethylamine or pyridine, preferably in a temperature range between −20° C. and room temperature possibly followed by Finkelstein reaction with sodium iodide in 2-butanone at reflux temperature or by treatment with trifluoromethanesulfonic anhydride/2,6-di-tert-butylpyridine in $CH_2Cl_2$ at 0° C. to give compounds 6 as methane-sulfonates, p-toluene-sulfonates, iodides or triflates, respectively (step f). Compounds of formula 6 can further be converted to amines 7 in solvents like DMA, DMF or dichloromethane via treatment with amines $R^{13}NH_2$ optionally using a protecting group and an additional base e.g. sodium hydride if BOC-protected amines are used (step g). All reactions described in scheme 6 are compatible with terminal alkynes, therefore in scheme 6 $R^{12}$ can also be a hydrogen atom.

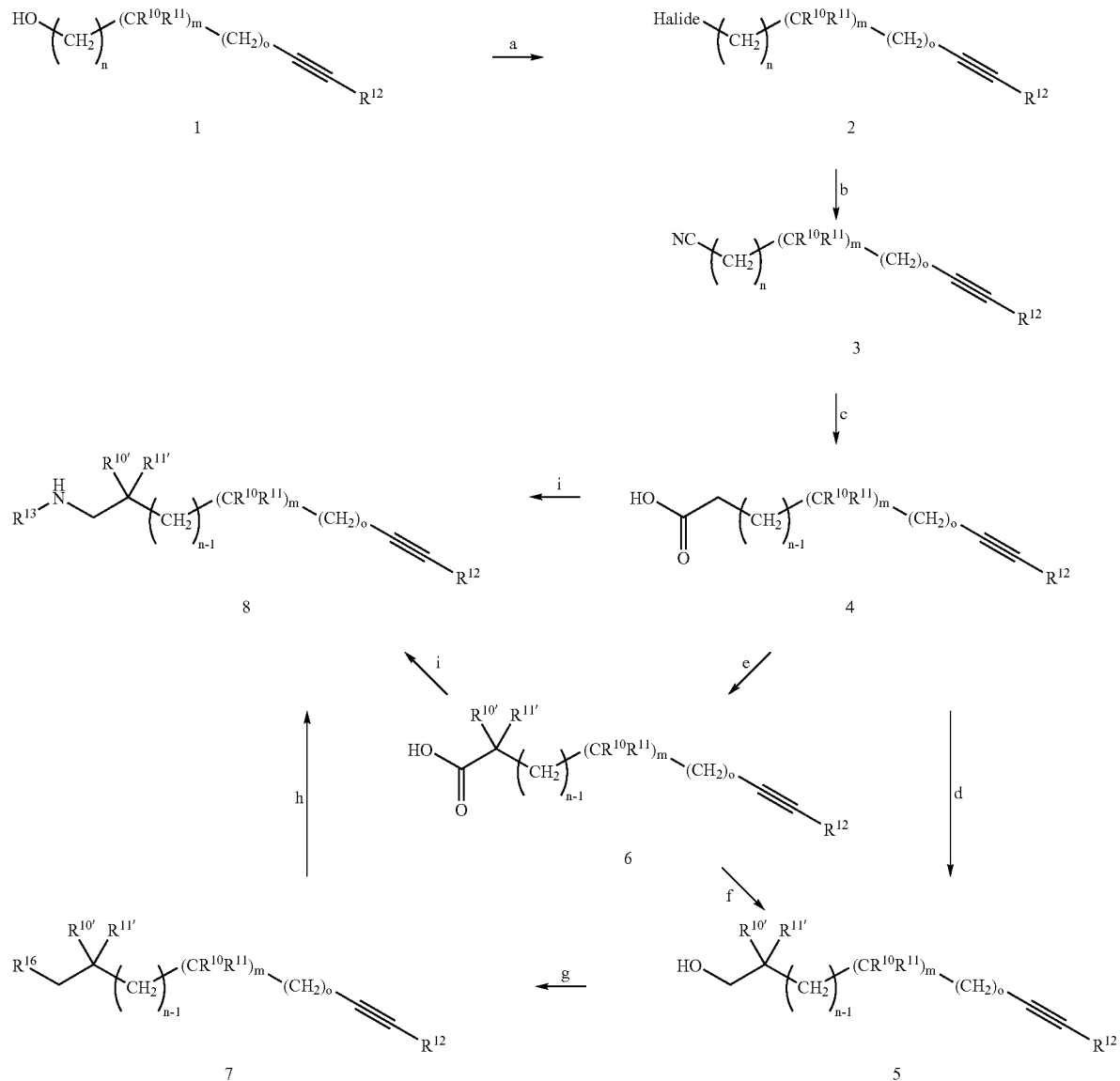

Scheme 7

Alcohols 1 (alcohols 2 in scheme 5 and alcohols 4 in scheme 6) comprising a chain length m, n and o can be converted into analogues with a chain length of m+1 or n+1 carbon atoms by methods well known in the art, e.g. by conversion of the primary hydroxy group of 1 into a suitable leaving group, e.g. a halide 2 (step a), followed by reaction with cyanide to form nitrites 3 (step b) and saponification to yield acids 4 (step c). Acids 4 can be further transformed into primary alcohols 5 ($R^{10'}=R^{11'}=H$), e.g. via esterification and subsequent lithiumaluminium hydride reduction (step d). Optionally, alcohols 5 can be elongated to a chain length of n+1 carbon atoms by repeating the reaction sequence described for the synthesis of alcohols 5 from alcohols 1. Alcohol compounds 5 containing one or more chiral centers can optionally be separated into optically pure enantiomers or diastereomers by methods well known in the art, e.g. via HPLC chromatography, chromatography on a chiral HPLC column, or by derivatization with an optically pure acid to form esters, which can be separated by conventional HPLC chromatography. Alpha mono- or di-substituted acids 6 ($R^{10'}$ and/or $R^{11'} \neq H$) can be synthesized via transforming acids 4 into the corresponding esters, treating them with a base like LDA or HMDS in solvents like tetrahydrofuran or 1,2-dimethoxyethane, followed by addition of one or sequentially two different alkyl halides, a reaction preferably performed between −78° C. and room temperature followed by ester hydrolysis to obtain acids 6 (step e). The corresponding esters of acids 6 can serve as starting materials for the introduction of additional substituents $R^{10'}$ and $R^{11'}$ as described in step c of scheme 6.

Compounds 6 can contain one or more stereocenters and can optionally be separated into optically pure enantiomers or diastereomers by methods well known in the art, e.g. by (chiral) HPLC chromatography, or by derivatization with an optically pure alcohol to form esters, which can be separated by conventional HPLC chromatography and then converted back to the enantiomerically pure acids 6. In addition, compounds 4 can be converted into chiral amides which can be used for asymmetric alkylation reactions being well known to a person skilled in the art. Esterification of acids 6 and subsequent lithiumaluminium hydride reduction gives alcohols 5 (step f). Alcohols 5 can be converted to activated building blocks of formula 7 ($R^{16}$=OMesylate, Op-Tosylate, Halide or Triflate), e.g. by treatment with methanesulfonyl chloride or p-toluenesulfonyl chloride in dichloromethane in the presence of a base like triethylamine or pyridine preferably in a temperature range between −20° C. and room temperature, optionally followed by Finkelstein reaction with sodium iodide in 2-butanone at reflux temperature or by treatment with trifluoromethanesulfonic anhydride/2,6-di-tert-butylpyridine in $CH_2Cl_2$ at 0° C. to give compounds 7 as methanesulfonates, p-toluene-sulfonates, iodides or triflates, respectively (step g). Compounds of formula 7 can further be converted to amines 8 in solvents like DMA, DMF or dichloromethane via treatment with amines $R^{13}NH_2$ optionally using a protecting group strategy (step h). Amines 8 can also be synthesized from acids 4 or 6 via formation of the corresponding amide which is subsequently reduced using methods well known to a person skilled in the art (step i). All reactions described in scheme 7 are compatible with terminal alkynes ($R^{12}$=H) except for step e where terminal alkynes need to be protected applying methods well known in the art, e.g. the use of a trimethylsilyl protection group.

The compounds of formula (I) and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula (I) and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula (I).

The following examples serve to illustrate the present invention in more detail. They are, however, not intended to limit its scope in any manner.

EXAMPLES

Abbreviations:

AcOEt=ethyl acetate, DIBAL-H=diisobutylaluminum hydride, DMF=N,N-dimethylformamide, DMPU=1,3-dimethyl-3,4,5,6-tetrahydro-2(1H)-pyrimidinone, DMSO=dimethyl sulfoxide, h=hour(s), HMDS=hexamethyl disilazane, HMPA=hexamethylphosphortriamide, HPLC=high performance liquid chromatography, LDA=lithium diisopropylamide, $PdCl_2(Ph_3P)_2$=dichlorobis (triphenylphosphine) palladium(II), $Pd(Ph_3P)_4$=tetrakis (triphenylphosphine)palladium, quant.=quantitative, RT=room temperature, THF=tetrahydrofuran.

Example 1 a] 5-(4-Trifluoromethoxy-phenyl)-pent-4-yn-1-ol

A mixture of 1-iodo-4-trifluoromethoxy-benzene (5 g, 17 mmol), $Pd(PPh_3)_4$ (973 mg, 1 mmol) and cuprous iodide (160 mg, 1 mmol) in piperidine (130 ml) was stirred for 30 min at 50° C. under an argon atmosphere. 4-Pentyn-1-ol (2.13 g, 25 mmol) was added within 60 min at 50° C. The temperature was raised to 80° C. and the mixture was stirred for 3 h at this temperature. The reaction mixture was cooled to ambient temperature, poured into a solution of saturated aqueous 10% KHSO$_4$/ice water 1/1 and extracted two times with tert butyl methyl ether. The combined extracts were washed with water and brine (two times) and dried over sodium sulfate. The solvent was removed under reduced pressure and the residue purified by column chromatography (silica gel, heptane/AcOEt) to give 3.4 g (13.9 mmol, 83%) of the title compound as orange oil.

MS: 244.2 (M)$^+$.

b] [6-(tert-Butyl-dimethyl-silanyloxy)-indol-1-yl]-acetic acid ethyl ester

To an ice cold solution of 6-(tert-butyl-dimethyl-silanyloxy)-1H-indole (1 g, 4.04 mmol) and cesium carbonate (1.45 g, 4.45 mmol) in DMF (10 ml) under an argon atmosphere was added bromo-acetic acid ethyl ester (490 µl, 4.45 mmol). The mixture was naturally warmed to room temperature, stirred for 14 h, poured onto 1 N HCl/ice water 1/1 and extracted two times with ethyl acetate. The combined organic layers were washed with water and dried over sodium sulfate. The solvent was removed under reduced pressure and the residue purified by column chromatography (silica gel, heptane/AcOEt) to give 1.2 g (3.6 mmol, 89%) of the title compound as yellow oil.

MS: 334.3 (M+H)$^+$.

c] (6-Hydroxy-indol-1-yl)-acetic acid ethyl ester

To an ice cold solution of [6-(tert-butyl-dimethyl-silanyloxy)-indol-1-yl]-acetic acid ethyl ester (1.15 g, 3.45 mmol) in THF (11.5 ml) was added a 1 M solution of tetrabutylammonium fluoride in THF (3.45 ml, 3.45 mmol) within 15 min. The reaction mixture was stirred for 1 h at ambient temperature, poured onto 1 N HCl/ice water 1/1 and extracted two times with ethyl acetate. The combined organic layers were washed with brine/ice water 1/1 and dried over sodium sulfate. The solvent was removed under reduced pressure and the residue purified by column chromatography (silica gel, heptane/AcOEt) to give 590 mg (2.7 mmol, 78%) of the title compound as colorless crystals.

MS: 219.0 (M)$^+$, 146.0.

d] {6-[5-(4-Trifluoromethoxy-phenyl)-pent-4-ynyloxy]-indol-1-yl}-acetic acid ethyl ester To an ice cold solution of (6-hydroxy-indol-1-yl)-acetic acid ethyl ester (100 mg, 455 µmol), 5-(4-trifluoromethoxyphenyl)-pent-4-yn-1-ol (111 mg, 455 µmol) and tributylphosphine (160 µl, 546 µmol) in tetrahydrofuran (10 ml) was added N,N,N',N'-tetramethyl azodicarboxamide (94 mg, 546 µmol). The cooling bath was removed and stirring continued for 14 h. The mixture was filtered over celite and the solvent removed under reduced pressure to give a yellow oil which was purified by column chromatography (silica gel, heptane/AcOEt) to obtain 65 mg (150 µmol, 32%) of the title compound as colorless oil.

MS: 446.0 (M+H)$^+$.

e] {6-[5-(4-Trifluoromethoxy-phenyl)-pent-4-ynyloxy]-indol-1-yl}-acetic acid

To a solution of {6-[5-(4-trifluoromethoxy-phenyl)-pent-4-ynyloxy]-indol-1-yl}-acetic acid ethyl ester (30 mg, 67 µmol) in THF/methanol 2/1 (1.5 ml) was added 1 N aqueous LiOH solution (400 µl). The reaction mixture was stirred for 14 h at ambient temperature and concentrated under reduced pressure. The residue was dissolved in 1 N HCl/ice water 1/1 and ethyl acetate, the layers were separated and the aqueous layer was extracted with ethyl acetate. The combined organic layers were washed with ice water/brine 1/1, dried over sodium sulfate and the solvent was evaporated in vacuo to give the title compound (28 mg, 67 µmol, quant.) as brown crystals.

MS: 418.3 (M+H)$^+$.

Example 2 a] 5-(3-Trifluoromethoxy-phenyl)-pent-4-yn-1-ol

In analogy to the procedure described in example 1 a], 1-iodo-3-trifluoromethoxy-benzene was reacted with 4-pentyn-1-ol in the presence of Pd(PPh$_3$)$_4$ and cuprous iodide to give the title compound as red oil.

MS: 245.3 (M+H)$^+$.

b] {6-[5-(3-Trifluoromethoxy-phenyl)-pent-4-ynyloxy]-indol-1-yl}-acetic acid ethyl ester In analogy to the procedure described for example 1 d], (6-hydroxy-indol-1-yl)-acetic acid ethyl ester (example 1 c]) was reacted with 5-(3-trifluoromethoxy-phenyl)-pent-4-yn-1-ol in the presence of N,N,N',N'-tetramethyl azodicarboxamide and tributylphosphine to give the title compound as colorless oil.

MS: 446.1 (M+H)$^+$.

c] {6-[5-(3-Trifluoromethoxy-phenyl)-pent-4-ynyloxy]-indol-1-yl}-acetic acid

In analogy to the procedure described for example 1 e], {6-[5-(3-trifluoromethoxy-phenyl)-pent-4-ynyloxy]-indol-1-yl}-acetic acid ethyl ester was treated with LiOH to obtain the title compound as green crystals.

MS: 418.4 (M+H)$^+$.

Example 3 a] 5-(4-Trifluoromethyl-phenyl)-pent-4-yn-1-ol

In analogy to the procedure described in example 1 a], 1-iodo-4-trifluoromethyl-benzene was reacted with 4-pentyn-1-ol in the presence of Pd(PPh$_3$)$_4$ and cuprous iodide to give the title compound as yellow oil.

MS: 228.2 (M)$^+$.

b] {6-[5-(4-Trifluoromethyl-phenyl)-pent-4-ynyloxy]-indol-1-yl}-acetic acid ethyl ester In analogy to the procedure described for example 1 d], (6-hydroxy-indol-1-yl)-acetic acid ethyl ester (example 1 c]) was reacted with 5-(4-trifluoromethyl-phenyl)-pent-4-yn-1-ol in the presence of N,N,N',N'-tetramethyl azodicarboxamide and tributylphosphine to give the title compound as yellow oil.

MS: 430.5 (M+H)$^+$.

c] {6-[5-(4-Trifluoromethyl-phenyl)-pent-4-yny-loxy]-indol-1-yl}-acetic acid

In analogy to the procedure described for example 1 e], {6-[5-(4-trifluoromethyl-phenyl)-pent-4-ynyloxy]-indol-1-yl}-acetic acid ethyl ester was treated with LiOH to obtain the title compound as off-white crystals.
MS: 402.5 (M+H)$^+$.

Example 4 a] 5-(3-Trifluoromethyl-phenyl)-pent-4-yn-1-ol

In analogy to the procedure described in example 1 a], 1-iodo-3-trifluoromethyl-benzene was reacted with 4-pentyn-1-ol in the presence of Pd(PPh$_3$)$_4$ and cuprous iodide to give the title compound as brown oil.
MS: 228.2 (M)$^+$.

b] {6-[5-(3-Trifluoromethyl-phenyl)-pent-4-yny-loxy]-indol-1-yl}-acetic acid ethyl ester In analogy to the procedure described for example 1 d], (6-hydroxy-indol-1-yl)-acetic acid ethyl ester (example 1 c]) was reacted with 5-(3-trifluoromethyl-phenyl)-pent-4-yn-1-ol in the presence of N,N,N',N'-tetramethyl azodicarboxamide and tributylphosphine to give the title compound as yellow oil.
MS: 430.5 (M+H)$^+$.

c] {6-[5-(3-Trifluoromethyl-phenyl)-pent-4-yny-loxy]-indol-1-yl}-acetic acid

In analogy to the procedure described for example 1 e], {6-[5-(3-trifluoromethyl-phenyl)-pent-4-ynyloxy]-indol-1-yl}-acetic acid ethyl ester was treated with LiOH to obtain the title compound as off-white crystals.
MS: 402.3 (M+H)$^+$.

Example 5 a] [4-(tert-Butyl-dimethyl-silanyloxy)-indol-1-yl]-acetic acid ethyl ester

In analogy to the procedure described in example 1 b], 4-(tert-butyl-dimethyl-silanyloxy)-1H-indole was reacted with bromo-acetic acid ethyl ester in the presence of cesium carbonate to give the title compound as yellow oil.

b] (4-Hydroxy-indol-1-yl)-acetic acid ethyl ester

In analogy to the procedure described in example 1 c], [4-(tert-butyl-dimethyl-silanyloxy)-indol-1-yl]-acetic acid ethyl ester was treated with tetrabutylammonium fluoride in THF to give the title compound as colorless crystals.
MS: 220.4 (M+H)$^+$.

c] {4-[5-(4-Trifluoromethoxy-phenyl)-pent-4-yny-loxy]-indol-1-yl}-acetic acid ethyl ester In analogy to the procedure described for example 1 d], (4-hydroxy-indol-1-yl)-acetic acid ethyl ester was reacted with 5-(4-trifluoromethoxy-phenyl)-pent-4-yn-1-ol in the presence of N,N,N',N'-tetramethyl azodicarboxamide and tributylphosphine to give the title compound as colorless crystals.
MS: 446.1 (M+H)$^+$.

d] {4-[5-(4-Trifluoromethoxy-phenyl)-pent-4-yny-loxy]-indol-1-yl}-acetic acid

In analogy to the procedure described for example 1 e], {4-[5-(4-trifluoromethoxy-phenyl)-pent-4-ynyloxy]-indol-1-yl}-acetic acid ethyl ester was treated with LiOH to obtain the title compound as colorless crystals.
MS: 416.4 (M−H)$^-$.

Example 6 a] 5-(tert-Butyl-dimethyl-silanyloxy)-1H-indole

A solution of 5-hydroxy-indole (5 g, 38 mmol), tert-butyldimethylsilyl chloride (6.13 g, 39.4 mmol) and imidazole (5.37 g, 68.1 mmol) in DMF (50 ml) was stirred for 20 h at RT. Diethyl ether was added and the mixture was washed with 1N HCl and water. The organic layer was dried over sodium sulfate and concentrated under reduced pressure to give 9.4 g (38 mmol, quant.) 5-(tert-butyl-dimethyl-silanyloxy)-1H-indole.
MS: 248.1 (M+H)$^+$.

b] [5-(tert-Butyl-dimethyl-silanyloxy)-indol-1-yl]-acetic acid ethyl ester

A suspension of 5-(tert-butyl-dimethyl-silanyloxy)-1H-indole (9.2 g, 37.2 mmol), ethyl bromoacetate (4.79 ml, 40.9 mmol) and cesium carbonate (36.4 g, 111.5 mmol) in DMF (140 ml) was stirred for 3 h at RT. Diethyl ether was added and the mixture was washed with 1N HCl and water, and dried over sodium sulfate. The ether phase was concentrated under reduced pressure to give 12.9 g (quant.) of [5-(tert-butyl-dimethyl-silanyloxy)-indol-1-yl]-acetic acid ethyl ester which was used in the next step without further purification.
MS: 334.1 (M+H)$^+$.

c] (5-Hydroxy-indol-1-yl)-acetic acid ethyl ester

To an ice cold solution of [5-(tert-butyl-dimethyl-silanyloxy)-indol-1-yl]-acetic acid ethyl ester (12.9 g, 38.7 mmol) in THF (130 ml) was added tetrabutylammonium fluoride hydrate (12.5 g, 38.7 mmol). The reaction mixture was stirred for 1 h at RT, diluted with diethyl ether and washed with 1N HCl and water. Evaporation of the solvent under reduced pressure gave 7.07 g (32.2 mmol, 83%) (5-hydroxy-indol-1-yl)-acetic acid ethyl ester.
MS: 220.1 (M+H)$^+$.

d] {5-[5-(4-Trifluoromethoxy-phenyl)-pent-4-yny-loxy]-indol-1-yl}-acetic acid ethyl ester In analogy to the procedure described for example 1 d], (5-hydroxy-indol-1-yl)-acetic acid ethyl ester was reacted with 5-(4-trifluoromethoxy-phenyl)-pent-4-yn-1-ol in the presence of N,N,N',N'-tetramethyl azodicarboxamide and tributylphosphine to give the title compound as yellow crystals.
MS: 446.1 (M+H)$^+$.

e] {5-[5-(4-Trifluoromethoxy-phenyl)-pent-4-yny-loxy]-indol-1-yl}-acetic acid

In analogy to the procedure described for example 1 e], {5-[5-(4-trifluoromethoxy-phenyl)-pent-4-ynyloxy]-indol-1-yl}-acetic acid ethyl ester was treated with LiOH to obtain the title compound as red crystals.
MS: 418.1 (M+H)$^+$.

Example 7 a] 2,2-Dimethyl-5-(4-trifluoromethoxy-phenyl)-pent-4-yn-1-ol

A mixture of 1-iodo-4-trifluoromethoxy-benzene (3.56 g, 12 mmol), Pd(PPh$_3$)$_4$ (578 mg, 0.5 mmol) and cuprous iodide (95 mg, 0.5 mmol) in piperidine (40 ml) was degassed (Ar) and stirred for 30 min at 50° C. under an argon atmosphere. 2,2-Dimethyl-pent-4-yn-1-ol (1.25 g, 10 mmol, 90% purity) [Magnus, Philip; Slater, Martin J.; Principe, Lawrence M. Journal of Organic Chemistry (1989), 54(21), 5148-5153] in piperidine (20 ml) was added within 60 min at 50° C. During the addition the oil bath temperature was slowly raised to 80° C. starting after 30 min. The mixture was stirred for 2 h at this temperature. The reaction mixture was cooled to ambient temperature, poured into a solution of aqueous 10% KHSO$_4$/ice water 1/1 and extracted two times with ether. The combined extracts were washed with aqueous 10% KHSO$_4$ and aqueous 10% NaCl and dried over sodium sulfate. The solvent was removed under reduced pressure and the residue purified by flash chromatography (silica gel, heptane/AcOEt 2:1 to 1:1) to give 1.91 g (7 mmol, 70%) of the title compound as yellow oil.

MS: 272.2 (M)$^+$.

b] {6-[2,2-Dimethyl-5-(4-trifluoromethoxy-phenyl)-pent-4-ynyloxy]-indol-1-yl}-acetic acid ethyl ester To an ice cold solution of 2,2-dimethyl-5-(4-trifluoromethoxy-phenyl)-pent-4-yn-1-ol (50 mg, 0.18 mmol) in dichloromethane (180 μl) was added trifluoromethanesulfonic anhydride (30 μl, 0.2 mmol) and 2,6-di-tert-butylpyridine (50 μl, 0.22 mmol) under an argon atmosphere. The reaction mixture was stirred for 2 h while the temperature rose from 0° C. to ambient temperature. The solvent was removed under reduced pressure and the residue dissolved in acetonitrile (0.6 ml). The obtained solution was added to a suspension of (6-hydroxy-indol-1-yl)-acetic acid ethyl ester (40 mg, 0.18 mmol; example 1 c]) and cesium carbonate (126 mg, 0.39 mmol) in acetonitrile (1.2 ml). The reaction mixture was stirred for 12 h at ambient temperature and for 1 h under reflux conditions. The residue was filtered off and washed with acetonitrile. The filtrate was brought to dryness under reduced pressure and the residue was dissolved in dichloromethane. The solvent was removed under reduced pressure and the remaining brown oil was purified by flash chromatography (silica gel, heptane/AcOEt) to give 35 mg (70 μmol, 40%) of the title compound as colorless oil.

MS: 474.3 (M+H)$^+$.

c] {6-[2,2-Dimethyl-5-(4-trifluoromethoxy-phenyl)-pent-4-ynyloxy]-indol-1-yl}-acetic acid In analogy to the procedure described for example 1 e], {6-[2,2-Dimethyl-5-(4-trifluoromethoxy-phenyl)-pent-4-ynyloxy]-indol-1-yl}-acetic acid ethyl ester was treated with LiOH to obtain the title compound as brown oil.

MS: 446.3 (M+H)$^+$.

Example 8 a] 5-(3-Trifluoromethoxy-phenyl)-pent-4-ynoic acid benzyl ester

To a degassed (Ar) solution of 1-iodo-3-trifluoromethoxy-benzene (0.54 ml, 3 mmol) in acetonitrile (30 ml) was added pent-4-ynoic acid benzyl ester (719 mg, 4 mmol; A. Rosowsky, R. A. Forsch, F. S. Queener, J. Med. Chem. 2003, 46, 1726-1736), PdCl$_2$(Ph$_3$P)$_2$ (122 mg, 0.17 mmol), cuprous iodide (33 mg, 0.17 mmol) and triethylamine (1.45 ml, 10 mmol). The reaction mixture was stirred for 2.5 h at ambient temperature, poured into a solution of aqueous 10% KHSO$_4$/ice water 1/1 and extracted two times with ether. The combined extracts were washed with aqueous 10% KHSO$_4$ and aqueous 10% NaCl and dried over sodium sulfate. The solvent was removed under reduced pressure and the residue purified by flash chromatography (silica gel, heptane/AcOEt) to give 1.13 g (3.2 mmol, 93%) of the title compound as yellow oil.

MS: 349.5 (M+H)$^+$.

b] 5-(3-Trifluoromethoxy-phenyl)-pent-4-ynoic acid

To a solution of 5-(3-trifluoromethoxy-phenyl)-pent-4-ynoic acid benzyl ester (500 mg, 1.4 mmol) in THF/methanol 2/1 (13.5 ml) was added 1 N aqueous LiOH solution (8.6 ml). The reaction mixture was stirred for 2 h at ambient temperature and concentrated under reduced pressure. The residue was dissolved in 1 N NaOH/ice water 1/1 and ethyl acetate and the layers were separated. The aqueous layer was brought to pH 1 with 1 N HCl and extracted two times with ethyl acetate. The combined extracts were washed with ice water/brine 1/1, dried over sodium sulfate and the solvent was evaporated in vacuo to give the title compound (370 mg, 1.4 mmol, quant.) as colorless crystals.

MS: 257.0 (M–H)$^-$.

c] {6-[5-(3-Trifluoromethoxy-phenyl)-pent-4-ynoylamino]-indol-1-yl}-acetic acid ethyl ester A mixture of (6-amino-indol-1-yl)-acetic acid ethyl ester (100 mg, 0.46 mmol; WO 2003041714 A1), 5-(3-trifluoromethoxy-phenyl)-pent-4-ynoic acid (115 mg, 0.44 mmol), 1-[3-(dimethylamino)-propyl]-3-ethylcarbodiimide hydrochloride (90 mg, 0.46 mmol) and 4-(dimethylamino)pyridine (57 mg, 0.46 mmol) in dichloromethane (1.5 ml) was stirred for 14 h at ambient temperature. The reaction mixture was diluted with dichloromethane, successively washed with 1 N HCl, brine, 1 N NaOH and brine, and dried over sodium sulfate. The solvent was removed under reduced pressure and the residue purified by flash chromatography (silica gel, heptane/AcOEt) to give 152 mg (0.33 mmol, 72%) of the title compound as off-white crystals.

MS: 459.4 (M+H)$^+$.

d] (6-{Methyl-[5-(3-trifluoromethoxy-phenyl)-pent-4-ynoyl]-amino}-indol-1-yl)-acetic acid {6-[5-(3-Trifluoromethoxy-phenyl)-pent-4-ynoylamino]-indol-1-yl}-acetic acid ethyl ester (50 mg, 0.11 mmol) was added to a suspension of sodium hydride (9 mg, 0.22 mmol) in tetrahydrofuran (1.5 ml) at 0° C. The mixture was stirred for 30 min at 0° C., methyl iodide (30 μl, 0.44 mmol) was added and stirring was continued for 14 h at ambient temperature. The suspension was cooled to 0° C., sodium hydride (13 mg, 0.33 mmol) and methyl iodide (45 μl, 0.66 mmol) were added and the mixture was stirred for 4 h at ambient temperature. Ethyl acetate was added, the solution was successively washed with brine, 1 N HCl/ice water 1/1 and brine and dried over sodium sulfate. The solvent was removed under reduced pressure to give 42 mg (0.09 mmol, 82%) of the title compound as yellow solid.
MS: 445.4 (M+H)$^+$.

Example 9 a] Methanesulfonic acid 5-(4-trifluoromethoxy-phenyl)-pent-4-ynyl ester

To an ice-cooled solution of 5-(4-trifluoromethoxy-phenyl)-pent-4-yn-1-ol (2.02 g, 8.3 mmol; example 1 a]) and Et$_3$N (1.73 ml, 12.4 mmol) in dichloromethane (100 ml) was added methanesulfonyl chloride (0.67 ml, 8.7 mmol) within 15 min keeping the temperature at 0-10° C. The reaction mixture was stirred at RT for 1 h 15 min. Water was added and after 5 min, the reaction was partitioned between ether and water. The aqueous layer was extracted again with ether (2×), the organic phases were washed with aqueous 10% NaCl, dried (Na$_2$SO$_4$) and concentrated to yield 2.5 g (7.7 mmol, 93%) of the title compound as light brown oil.
MS: 322.1 (M)$^+$.

b] {6-[5-(4-Trifluoromethoxy-phenyl)-pent-4-ynylamino]-indol-1-yl}-acetic acid ethyl ester A suspension of (6-amino-indol-1-yl)-acetic acid ethyl ester (50 mg, 0.23 mmol, WO 2003041714 A1), methanesulfonic acid 5-(4-trifluoromethoxy-phenyl)-pent-4-ynyl ester (148 mg, 0.46 mmol) and potassium carbonate (63 mg, 0.46 mmol) in DMF (1 ml) was stirred for 3 h at ambient temperature and for 14 h at 70° C. The reaction mixture was poured onto ethyl acetate/ice water 1/1, the layers were separated and the aqueous layer was extracted two times with ethyl acetate. The combined extracts were washed with brine, dried over sodium sulfate and the solvent was removed under reduced pressure. The residue was purified by flash chromatography (silica gel, heptane/AcOEt) to give 16 mg (0.03 mmol, 15%) of the title compound as yellow oil.
MS: 445.4 (M+H)$^+$.

c] {6-[5-(4-Trifluoromethoxy-phenyl)-pent-4-ynylamino]-indol-1-yl}-acetic acid

In analogy to the procedure described for example 1 e], {6-[5-(4-trifluoromethoxy-phenyl)-pent-4-ynylamino]-indol-1-yl}-acetic acid ethyl ester was treated with LiOH to obtain the title compound as green solid.
MS: 415.2 (M–H)$^-$.

Example 10 a] 5-(4-Trifluoromethoxy-phenyl)-pent-4-ynoic acid methyl ester

In analogy to the procedure described for example 8 a], pent-4-ynoic acid methyl ester (W. D. Wulff, S. J. McCallum, F. A. Kunng, J. Am. Chem. Soc. 1988, 110, 7419-7434) was reacted with 1-iodo-4-trifluoromethoxy-benzene in the presence of PdCl$_2$(Ph$_3$P)$_2$ and cuprous iodide to give the title compound as brown oil.
MS: 272.1 (M)$^+$.

b] 5-(4-Trifluoromethoxy-phenyl)-pent-4-ynoic acid

In analogy to the procedure described for example 1 e], 5-(4-trifluoromethoxy-phenyl)-pent-4-ynoic acid methyl ester was treated with LiOH to obtain the title compound as brown crystals.
MS: 256.9 (M–H)$^-$.

c] {6-[5-(4-Trifluoromethoxy-phenyl)-pent-4-ynoylamino]-indol-1-yl}-acetic acid ethyl ester In analogy to the procedure described in example 8 c], (6-amino-indol-1-yl)-acetic acid ethyl ester (WO 2003041714 A1) was reacted with 5-(4-trifluoromethoxy-phenyl)-pent-4-ynoic acid in the presence of 1-[3-(dimethylamino)-propyl]-3-ethylcarbodiimide hydrochloride and 4-(dimethylamino)pyridine to give the title compound as brown crystals.
MS: 459.5 (M+H)$^+$.

d] (6-{Methyl-[5-(4-trifluoromethoxy-phenyl)-pent-4-ynoyl]-amino}-indol-1-yl)-acetic acid In analogy to the procedure described in example 8 d], {6-[5-(4-trifluoromethoxy-phenyl)-pent-4-ynoylamino]-indol-1-yl}-acetic acid ethyl ester was reacted with methyl iodide in the presence of sodium hydride to give the title compound as brown liquid.
MS: 443.4 (M–H)$^-$.

Example 11 a] [7-(tert-Butyl-dimethyl-silanyloxy)-indol-1-yl]-acetic acid ethyl ester

In analogy to the procedure described in example 6 b], 7-(tert-butyl-dimethyl-silanyloxy)-1H-indole (EP 206225 A2) was reacted with ethyl bromoacetate in the presence of cesium carbonate in acetonitrile to give the title compound as colorless liquid.
MS: 334.1 (M+H)$^+$.

b] (7-Hydroxy-indol-1-yl)-acetic acid ethyl ester

In analogy to the procedure described in example 6 c], [7-(tert-butyl-dimethyl-silanyloxy)-indol-1-yl]-acetic acid ethyl ester was treated with tetrabutylammonium fluoride hydrate to give the title compound as colorless solid.
MS: 220.1 (M+H)$^+$.

c] {7-[5-(4-Trifluoromethoxy-phenyl)-pent-4-ynyloxy]-indol-1-yl}-acetic acid ethyl ester A suspension of (7-hydroxy-indol-1-yl)-acetic acid ethyl ester (50 mg, 0.23 mmol), methanesulfonic acid 5-(4-trifluoromethoxy-phenyl)-pent-4-ynyl ester (74 mg, 0.23 mmol; example 9 a]), cesium carbonate (82 mg, 0.25 mmol) and a trace of potassium iodide in acetonitrile (2.5 ml) was stirred for 14 h at ambient temperature and for 4 h at 50° C. The reaction mixture was poured onto 1 N HCl/ice water 1/1 and extracted two times with ethyl acetate. The combined extracts were washed with brine, dried over sodium sulfate and the solvent was removed under reduced pressure. The residue was purified by flash chromatography (silica gel, heptane/AcOEt) to give 16 mg (0.04 mmol, 16%) of the title compound as colorless oil.
MS: 446.3 (M+H)$^+$.

d] {7-[5-(4-Trifluoromethoxy-phenyl)-pent-4-yny-loxy]-indol-1-yl}-acetic acid

In analogy to the procedure described for example 1 e], {7-[5-(4-trifluoromethoxy-phenyl)-pent-4-ynyloxy]-indol-1-yl}-acetic acid ethyl ester was treated with LiOH to obtain the title compound as brown liquid.

MS: 418.1 (M+H)$^+$.

Example 12 a] [rac]-2-{6-[5-(4-Trifluoromethoxy-phenyl)-pent-4-ynyloxy]-indol-1-yl}-propionic acid ethyl ester In analogy to the procedure described in example 11 c], [rac]-2-(6-hydroxy-indol-1-yl)-propionic acid ethyl ester (GB 2253848 A1) was reacted with methanesulfonic acid 5-(4-trifluoromethoxy-phenyl)-pent-4-ynyl ester (example 9 a]) in the presence of cesium carbonate and potassium iodide to give the title compound as colorless liquid.

MS: 460.4 (M+H)$^+$.

b] [rac]-2-{6-[5-(4-Trifluoromethoxy-phenyl)-pent-4-ynyloxy]-indol-1-yl}-propionic acid In analogy to the procedure described for example 1 e], [rac]-2-{6-[5-(4-trifluoromethoxy-phenyl)-pent-4-ynyloxy]-indol-1-yl}-propionic acid ethyl ester was treated with LiOH to obtain the title compound as yellow oil.

MS: 432.5 (M+H)$^+$.

Example 13 a] 2-(1H-Indol-6-yl)-N-prop-2-ynyl-acetamide

Hydroxybenzotriazole (614 mg, 4.5 mmol), 4-ethylmorpholine (320 μl, 2.5 mmol), propargylamine (160 μl, 2.5 mmol) and 1-[3-(dimethylamino)-propyl]-3-ethylcarbodiimide hydrochloride (523 mg, 2.7 mmol) were added to an ice cold solution of (1H-indol-6-yl)-acetic acid (640 mg, 2.2 mmol; U.S. Pat. No. 4,894,386 A) in tetrahydrofuran (6.4 ml). The solution was naturally warmed to ambient temperature and stirred for 14 h. Ice water/brine 1/1 was added and the mixture was extracted two times with dichloromethane. The combined extracts were successively washed with 1 N HCl, brine, 1 N NaOH and brine, and dried over sodium sulfate. The solvent was removed under reduced pressure to give brown crystals which were recrystallized from heptane/dichloromethane to give 380 mg (1.8 mmol, 80%) of the title compound as colorless crystals.

MS: 213.4 (M+H)$^+$.

b] 2-(1H-Indol-6-yl)-N-[3-(4-trifluoromethoxy-phenyl)-prop-2-ynyl]-acetamide

In analogy to the procedure described for example 8 a], 2-(1H-indol-6-yl)-N-prop-2-ynyl-acetamide was reacted with 4-(trifluoromethoxy)-iodobenzene in the presence of PdCl$_2$(Ph$_3$P)$_2$ and cuprous iodide to give the title compound as colorless crystals.

MS: 373.0 (M+H)$^+$.

c] (6-{[3-(4-Trifluoromethoxy-phenyl)-prop-2-ynyl-carbamoyl]-methyl}-indol-1-yl)-acetic acid ethyl ester In analogy to the procedure described for example 1 b], 2-(1H-indol-6-yl)-N-[3-(4-trifluoromethoxy-phenyl)-prop-2-ynyl]-acetamide was reacted with bromo-acetic acid ethyl ester in the presence of cesium carbonate and potassium iodide in acetonitrile under reflux conditions to give the title compound as off-white solid.

MS: 459.1 (M+H)$^+$.

d] (6-{[3-(4-Trifluoromethoxy-phenyl)-prop-2-ynyl-carbamoyl]-methyl}-indol-1-yl)-acetic acid In analogy to the procedure described for example 1 e], (6-{[3-(4-trifluoromethoxy-phenyl)-prop-2-ynylcarbamoyl]-methyl}-indol-1-yl)-acetic acid ethyl ester was treated with LiOH to obtain the title compound as off-white solid.

MS: 431.4 (M+H)$^+$.

Example 14 a] 2-(1H-Indol-6-yl)-N-[3-(4-trifluoromethyl-phenyl)-prop-2-ynyl]-acetamide

In analogy to the procedure described for example 8 a], 2-(1H-indol-6-yl)-N-prop-2-ynyl-acetamide (example 13 a]) was reacted with 4-iodobenzotrifluoride in the presence of PdCl$_2$(Ph$_3$P)$_2$ and cuprous iodide to give the title compound as colorless crystals.

MS: 357.1 (M+H)$^+$.

b] (6-{[3-(4-Trifluoromethyl-phenyl)-prop-2-ynyl-carbamoyl]-methyl}-indol-1-yl)-acetic acid ethyl ester In analogy to the procedure described for example 1 b], 2-(1H-indol-6-yl)-N-[3-(4-trifluoromethyl-phenyl)-prop-2-ynyl]-acetamide was reacted with bromo-acetic acid ethyl ester in the presence of cesium carbonate and potassium iodide in acetonitrile under reflux conditions to give the title compound as colorless oil.

MS: 443.5 (M+H)$^+$.

c] (6-{[3-(4-Trifluoromethyl-phenyl)-prop-2-ynyl-carbamoyl]-methyl}-indol-1-yl)-acetic acid In analogy to the procedure described for example 1 e], (6-{[3-(4-trifluoromethyl-phenyl)-prop-2-ynylcarbamoyl]-methyl}-indol-1-yl)-acetic acid ethyl ester was treated with LiOH to obtain the title compound as off-white crystals.

MS: 415.3 (M+H)$^+$.

Example 15 a] 5-(4-Trifluoromethyl-phenyl)-pent-4-ynoic acid benzyl ester

In analogy to the procedure described for example 8 a], pent-4-ynoic acid benzyl ester (Rosowsky, Andre; Forsch, Ronald A.; Queener, Sherry F., Journal of Medicinal Chemistry (2003), 46(9), 1726-1736) was reacted with 4-iodobenzotrifluoride in the presence of PdCl$_2$(Ph$_3$P)$_2$ and cuprous iodide to give the title compound as yellow oil.

MS: 332.1 (M)$^+$.

b] 5-(4-Trifluoromethyl-phenyl)-pent-4-ynoic acid

In analogy to the procedure described for example 1 e], 5-(4-trifluoromethyl-phenyl)-pent-4-ynoic acid benzyl ester was treated with LiOH to obtain the title compound as off-white solid.
MS: 241.2 (M−H)⁻.

c] 5-(4-Trifluoromethyl-phenyl)-pent-4-ynoic acid (1H-indol-6-ylmethyl)-amide

In analogy to the procedure described for example 13 a], 5-(4-trifluoromethyl-phenyl)-pent-4-ynoic acid was reacted with 6-aminoethyl-1H-indole in the presence of 1-hydroxybenzotriazole, 4-ethylmorpholine and 1-[3-(dimethylamino)-propyl]-3-ethylcarbodiimide hydrochloride to give the title compound as colorless crystals.
MS: 371.1 (M+H)⁺.

d] (6-{[5-(4-Trifluoromethyl-phenyl)-pent-4-ynoylamino]-methyl}-indol-1-yl)-acetic acid ethyl ester In analogy to the procedure described for example 1 b], 5-(4-trifluoromethyl-phenyl)-pent-4-ynoic acid (1H-indol-6-ylmethyl)-amide was reacted with bromo-acetic acid ethyl ester in the presence of cesium carbonate and potassium iodide in acetonitrile under reflux conditions to give the title compound as off-white crystals.
MS: 457.5 (M+H)⁺.

e] [6-({Methyl-[5-(4-trifluoromethyl-phenyl)-pent-4-ynoyl]-amino}-methyl)-indol-1-yl]-acetic acid In analogy to the procedure described in example 8 d], (6-{[5-(4-trifluoromethyl-phenyl)-pent-4-ynoylamino]-methyl}-indol-1-yl)-acetic acid ethyl ester was reacted with methyl iodide in the presence of sodium hydride to give the title compound as yellow foam.
MS: 443.5 (M+H)⁺.

Example 16 a] [3-(4-Trifluoromethoxy-phenyl)-prop-2-ynyl]-carbamic acid tert-butyl ester

In analogy to the procedure described for example 8 a], tert-butyl 2-propynylcarbamate was reacted with 1-iodo-4-trifluoromethoxy-benzene in the presence of PdCl$_2$(Ph$_3$P)$_2$ and cuprous iodide to give the title compound as yellow crystals.
MS: 315.2 (M)⁺.

b] Methyl-[3-(4-trifluoromethoxy-phenyl)-prop-2-ynyl]-carbamic acid tert-butyl ester

[3-(4-Trifluoromethoxy-phenyl)-prop-2-ynyl]-carbamic acid tert-butyl ester (500 mg, 1.6 mmol) was added to an ice cold solution of iodomethane (100 μl, 1.7 mmol) and sodium hydride (73 mg, 1.7 mmol; 55% suspension in mineral oil) in DMF (5 ml). The reaction mixture was stirred for 5 h at ambient temperature, cooled to 0° C. and carefully quenched with saturated aqueous ammonium chloride solution. Ice water/ethyl acetate 1/1 were added, the layers were separated and the aqueous layer was extracted two times with ethyl acetate. The combined extracts were washed with brine and dried over sodium sulfate. The solvent was removed under reduced pressure and the residue was purified by flash chromatography (silica gel, heptane/AcOEt) to give 258 mg (0.8 mmol, 49%) of the title compound as yellow oil.
MS: 330.2 (M+H)⁺.

c] Methyl-[3-(4-trifluoromethoxy-phenyl)-prop-2-ynyl]-amine

A 4 M solution of HCl in dioxane (330 μl, 1 mmol) was added at ambient temperature to a solution of methyl-[3-(4-trifluoromethoxy-phenyl)-prop-2-ynyl]-carbamic acid tert-butyl ester (50 mg, 0.15 mmol) in dichloromethane (0.5 ml). The reaction mixture was stirred for 3 h at ambient temperature. The solvent was removed under reduced pressure and the residue crystallized from dichloromethane/heptane to yield 20 mg (90 μmol, 57%) of the title compound as brown crystals.
MS: 230.3 (M+H)⁺.

d] 2-(1H-Indol-6-yl)-N-methyl-N-[3-(4-trifluoromethoxy-phenyl)-prop-2-ynyl]-acetamide In analogy to the procedure described for example 13 a], (1H-indol-6-yl)-acetic acid (U.S. Pat. No. 4,894,386 A) was reacted with methyl-[3-(4-trifluoromethoxy-phenyl)-prop-2-ynyl]-amine in the presence of 1-hydroxybenzotriazole, 4-ethylmorpholine and 1-[3-(dimethylamino)-propyl]-3-ethylcarbodiimide hydrochloride to give the title compound as orange oil.
MS: 387.1 (M+H)⁺.

e] [6-({Methyl-[3-(4-trifluoromethoxy-phenyl)-prop-2-ynyl]-carbamoyl}-methyl)-indol-1-yl]-acetic acid ethyl ester In analogy to the procedure described for example 1 b], 2-(1H-indol-6-yl)-N-methyl-N-[3-(4-trifluoromethoxy-phenyl)-prop-2-ynyl]-acetamide was reacted with bromo-acetic acid ethyl ester in the presence of cesium carbonate and potassium iodide in acetonitrile under reflux conditions to give the title compound as orange crystals.
MS: 473.0 (M+H)⁺.

f] [6-({Methyl-[3-(4-trifluoromethoxy-phenyl)-prop-2-ynyl]-carbamoyl}-methyl)-indol-1-yl]-acetic acid In analogy to the procedure described for example 1 e], [6-({methyl-[3-(4-trifluoromethoxy-phenyl)-prop-2-ynyl]-carbamoyl}-methyl)-indol-1-yl]-acetic acid ethyl ester was treated with LiOH to obtain the title compound as yellow crystals.
MS: 443.4 (M−H)⁻.

Example 17 a] 5-(4-Trifluoromethoxy-phenyl)-pent-4-ynoic acid methoxy-methyl-amide

To a solution of 5-(4-trifluoromethoxy-phenyl)-pent-4-ynoic acid (1.0 g, 3.87 mmol; example 10 b]) in CH$_2$Cl$_2$ (50 ml) was added N,O-dimethylhydroxylamine hydrochloride (0.45 g, 4.65 mmol) and N-methylmorpholine (0.55 ml, 5 mmol). The mixture was cooled to 0° C. and N-(3-dimethylaminopropyl)-N'-ethylcarbodiimide hydrochloride (0.97 g, 5 mmol) was added. The reaction solution was naturally warmed to ambient temperature, stirred over night and partitioned between aqueous 10% KHSO$_4$/ether (three times). The organic phases were washed with aqueous saturated NaHCO₃, aqueous 10% NaCl and dried (Na₂SO₄) to give 1.165 g (3.86 mmol, quant.) of the title compound as brown oil.

MS: 302.1 (M+H)⁺.

b] 6-(4-Trifluoromethoxy-phenyl)-hex-5-yn-2-one

A solution of methyl magnesium bromide (1.11 ml, 3.32 mmol; 3 M solution in ether) in ether (4 ml) was added dropwise to an ice cold solution of 5-(4-trifluoro-methoxy-phenyl)-pent-4-ynoic acid methoxy-methyl-amide (0.77 g, 2.56 mmol) in ether (4 ml). The reaction mixture was stirred for 3 h at 0° C., diluted with ether and washed with ice cold aqueous, saturated NH₄Cl solution, aqueous 10% KHSO₄ and aqueous 10% NaCl solution. The water phases were extracted with ether (two times), the combined organic layers were dried (Na₂SO₄) and evaporated to give 0.68 g (quant.) of the title compound as yellow oil which was used in the next step without further purification.

MS: 256.1 (M+H)⁺.

c] [rac]-6-(4-Trifluoromethoxy-phenyl)-hex-5-yn-2-ol

DIBAL-H (1.46 ml, 1.75 mmol; 1.2 M solution in toluene) was added dropwise within 15 min to a dry ice cooled (−30° C.) solution of 6-(4-trifluoromethoxy-phenyl)-hex-5-yn-2-one (0.23 g, 0.88 mmol) in THF (4 ml). The reaction was warmed to 0° C. over a time period of 1 h 10 min and neutralized with aqueous 10% KHSO₄ solution. The mixture was extracted with ether (three times), the combined organic layers were washed with aqueous 10% NaCl solution, dried (Na₂SO₄) and evaporated to give 0.24 g (quant.) of the title compound as light brown oil.

MS: 258.1 (M)⁺.

d] [rac]-{6-[1-Methyl-5-(4-trifluoromethoxy-phenyl)-pent-4-ynyloxy]-indol-1-yl}-acetic acid ethyl ester In analogy to the procedure described for example 1 d], (6-hydroxy-indol-1-yl)-acetic acid ethyl ester (example 1 c]) was reacted with [rac]-6-(4-trifluoromethoxy-phenyl)-hex-5-yn-2-ol in the presence of N,N,N',N'-tetramethyl azodicarboxamide and tributylphosphine to give the title compound as colorless oil.

MS: 460.4 (M+H)⁺.

e] [rac]-{6-[1-Methyl-5-(4-trifluoromethoxy-phenyl)-pent-4-ynyloxy]-indol-1-yl}-acetic acid In analogy to the procedure described for example 1 e], [rac]-{6-[1-methyl-5-(4-trifluoromethoxy-phenyl)-pent-4-ynyloxy]-indol-1-yl}-acetic acid ethyl ester was treated with LiOH to obtain the title compound as brown crystals.

MS: 430.3 (M−H)⁻.

Example 18

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution/suspension of the above mentioned film coat.

Example 19

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 20

Injection solutions can have the following composition:

| | |
|---|---|
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example 21

Soft gelatin capsules containing the following ingredients can be manufactured in a conventional manner:

| Capsule contents | |
| --- | --- |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example 22

Sachets containing the following ingredients can be manufactured in a conventional manner:

| | |
| --- | --- |
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Example 23

The following tests were carried out in order to determine the activity of the compounds of formula (I).

Background information on the performed assays can be found in: Nichols J S et al. "Development of a scintillation proximity assay for peroxisome proliferator-activated receptor gamma ligand binding domain", (1998) Anal. Biochem. 257: 112-119.

Full-length cDNA clones for humans PPARδ and PPARα and mouse PPARγ were obtained by RT-PCR from human adipose and mouse liver cRNA, respectively, cloned into plasmid vectors and verified by DNA sequencing. Bacterial and mammalian expression vectors were constructed to produce glutathione-s-transferase (GST) and Gal4 DNA binding domain proteins fused to the ligand binding domains (LBD) of PPARδ (aa 139 to 442), PPARγ (aa 174 to 476) and PPARα (aa 167 to 469). To accomplish this, the portions of the cloned sequences encoding the LBDs were amplified from the full-length clones by PCR and then subcloned into the plasmid vectors. Final clones were verified by DNA sequence analysis.

Induction, expression, and purification of GST-LBD fusion proteins were performed in E. coli strain BL21(pLysS) cells by standard methods (Ref: Current Protocols in Molecular Biology, Wiley Press, edited by Ausubel et al.).

Radioligand Binding Assay

PPARδ receptor binding was assayed in HNM10 (50 mM Hepes, pH 7.4, 10 mM NaCl, 5 mM $MgCl_2$, 0.15 mg/ml fatty acid-free BSA and 15 mM DTT). For each 96 well reaction a 500 ng equivalent of GST-PPARδ-LBD fusion protein and radioligand, e.g. 20000 dpm {2-methyl-4-[4-methyl-2-(4-trifluoromethyl-phenyl)-thiazol-5-yl-ditritiomethylsulfanyl]-phenoxy}-acetic acid, was bound to 10 μg SPA beads (PharmaciaAmersham) in a final volume of 50 μl by shaking. The resulting slurry was incubated for 1 h at RT and centrifuged for 2 min at 1300 g. The supernatant containing unbound protein was removed and the semidry pellet containing the receptor-coated beads was resuspended in 50 ul of HNM. Radioligand was added and the reaction incubated at RT for 1 h and scintillation proximity counting performed in the presence of test compounds was determined. All binding assays were performed in 96 well plates and the amount of bound ligand was measured on a Packard TopCount using OptiPlates (Packard). Dose response curves were done in triplicates within a range of concentration from $10^{-10}$ M to $10^{-4}$ M.

PPARα receptor binding was assayed in TKE50 (50 mM Tris-HCl, pH 8, 50 mM KCl, 2 mM EDTA, 0.1 mg/ml fatty acid-free BSA and 10 mM DTT). For each 96 well reaction an 140 ng equivalent of GST-PPARα-LBD fusion protein was bound to 10 μg SPA beads (PharmaciaAmersham) in a final volume of 50 μl by shaking. The resulting slurry was incubated for 1 h at RT and centrifuged for 2 min at 1300 g. The supernatant containing unbound protein was removed and the semidry pellet containing the receptor-coated beads was resolved in 50 μl of TKE. For radioligand binding e.g. 10000 dpm of 2(S)-(2-benzoyl-phenylamino)-3-{4-[1,1-ditritio-2-(5-methyl-2-phenyl-oxazol-4-yl)-ethoxy]-phenyl}-propionic acid or 2,3-ditritio-2(S)-methoxy-3-{4-[2-(5-methyl-2-phenyl-oxazol-4-yl)-ethoxy]-benzo[b]thiophen-7-yl}-propionic acid in 50 ul were added, the reaction incubated at RT for 1 h and scintillation proximity counting performed. All binding assays were performed in 96 well plates and the amount of bound ligand measured on a Packard TopCount using OptiPlates (Packard). Nonspecific binding was determined in the presence of $10^{-4}$ M unlabelled compound. Dose response curves were done in triplicates within a range of concentration from $10^{-10}$ M to $10^{-4}$ M.

PPARγ receptor binding was assayed in TKE50 (50 mM Tris-HCl, pH 8, 50 mM KCl, 2 mM EDTA, 0.1 mg/ml fatty acid-free BSA and 10 mM DTT). For each 96 well reaction an 140 ng equivalent of GST-PPARγ-LBD fusion protein was bound to 10 μg SPA beads (PharmaciaAmersham) in a final volume of 50 ul by shaking. The resulting slurry was incubated for 1 h at RT and centrifuged for 2 min at 1300 g. The supernatant containing unbound protein was removed and the semidry pellet containing the receptor-coated beads was resolved in 50 ul of TKE. For radioligand binding e.g. 10000 dpm 2(S)-(2-benzoyl-phenylamino)-3-{4-[1,1-ditritio-2-(5-methyl-2-phenyl-oxazol-4-yl)-ethoxy]-phenyl}-propionic acid in 50 μl were added, the reaction incubated at RT for 1 h and scintillation proximity counting performed. All binding assays were performed in 96 well plates and the amount of bound ligand measured on a Packard TopCount using OptiPlates (Packard). Nonspecific binding was determined in the presence of $10^{-4}$ M unlabelled compound. Dose response curves were done in triplicates within a range of concentration from $10^{-10}$ M to $10^{-4}$ M.

Luciferase Transcriptional Reporter Gene Assays

Baby hamster kidney cells (BHK21 ATCC CCL10) were grown in DMEM medium containing 10% FBS at 37° C. in a 95% O2:5% CO$_2$ atmosphere. Cells were seeded in 6 well plates at a density of $10^5$ Cells/well and then batch-transfected with either the pFA-PPARδ-LBD, pFA-PPARγ-LBD or pFA-PPARα-LBD expression plasmids plus a reporter plasmid. Transfection was accomplished with the Fugene 6 reagent (Roche Molecular Biochemicals) according to the suggested protocol. Six hours following transfection, the cells were harvested by trypsinization and seeded in 96 well plates at a density of $10^4$ cells/well. After 24 hours to allow attachment of cells, the medium was removed and replaced with 100 ul of phenol red-free medium containing the test substances or control ligands (final DMSO concentration: 0.1%). Following incubation of the cells for 24 hours with substances, 50 μl of the supernatant was discarded and then 50 μl of Luciferase Constant-Light Reagent (Roche Molecular Biochemicals) to lyse the cells and initiate the luciferase reaction was added. Luminescence for luciferase was measured in a Packard TopCount. Transcriptional activation in the presence of a test substance was expressed as fold-activation over cells incubated in the absence of the substance. EC50 values were calculated using the XLfit program (ID Business Solutions Ltd. UK).

The free acids of the compounds of the present invention ($R^1$ is hydrogen) exhibit IC$_{50}$ values of 0.1 nM to 10 μM, preferably 1 nM to 500 nM for PPARδ and/or IC$_{50}$ values of 1 nM to 10 μM, preferably 10 nM to 500 nM for PPARα. Compounds, in which $R^1$ is not hydrogen are converted in vivo to compounds in which $R^1$ is hydrogen. The following table shows measured values for some selected compounds of the present invention.

|  | PPARα IC$_{50}$ (μmol/l) | PPARγ IC$_{50}$ (μmol/l) | PPARδ IC$_{50}$ (μmol/l) |
| --- | --- | --- | --- |
| Example 2 | 0.317 | >10 | 0.149 |
| Example 6 | 0.074 | >10 | 0.301 |

It is to be understood that the invention is not limited to the particular embodiments of the invention described above, as variations of the particular embodiments may be made and still fall within the scope of the appended claims.

What is claimed is:

1. A compound of the formula (I):

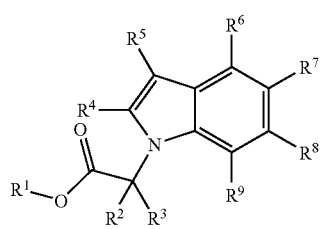

I wherein:
$R^1$ is hydrogen or $C_{1-7}$-alkyl;

$R^2$ and $R^3$ independently from each other are selected from the group consisting of hydrogen, $C_{1-7}$-alkyl and $C_{1-7}$-alkyl-$C_{1-7}$-alkoxy;

$R^4$ and $R^5$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, fluoro-$C_{1-7}$-alkoxy, cyano-$C_{1-7}$-alkyl and cyano;

$R^6$, $R^7$, $R^8$ and $R^9$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, fluoro-$C_{1-7}$-alkoxy, cyano-$C_{1-7}$-alkyl and cyano;

and one of $R^6$, $R^7$, $R^8$ and $R^9$ is

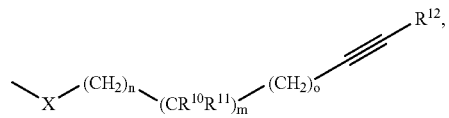

wherein:
X is selected from the group consisting of S, O, NR$^{13}$, (CH$_2$)$_p$NR$^{13}$CO and (CH$_2$)$_p$CONR$^{13}$, $R^{13}$ is selected from the group consisting of hydrogen, $C_{1-7}$-alkyl, $C_{3-7}$-cycloalkyl, fluoro-$C_{1-7}$-alkyl, hydroxy-$C_{2-7}$-alkyl and $C_{1-7}$-alkoxy-$C_{2-7}$-alkyl;

$R^{10}$ is selected from the group consisting of $C_{1-7}$-alkyl, $C_{3-7}$-cycloalkyl, fluoro-$C_{1-7}$-aklyl and $C_{1-7}$-alkoxy-$C_{1-7}$-alkyl;

$R^{11}$ is selected from the group consisting of hydrogen, $C_{1-7}$-alkyl and $C_{1-7}$-alkoxy-$C_{1-7}$-alkyl;

or $R^{10}$ and $R^{11}$ together with the carbon atom they are attached to form a $C_{3-6}$-cycloalkyl ring;

$R^{12}$ is aryl or heteroaryl;

m, o, p is 0, 1 or 2; n is 0, 1, 2 or 3 and the sum of m, n and o is 1 to 5; and pharmaceutically acceptable salts and/or esters thereof.

2. The compound according to claim 1 having the formula (I-A):

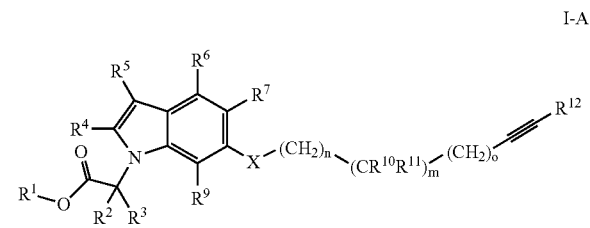

I-A wherein:
X, $R^1$ to $R^5$, $R^{10}$ to $R^{12}$, m, n and o are as defined herein before;

$R^6$, $R^7$ and $R^9$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, fluoro-$C_{1-7}$-alkoxy, cyano-$C_{1-7}$-alkyl and cyano; and pharmaceutically acceptable salts and/or esters thereof.

3. The compound according to claim 1, wherein $R^6$, $R^7$ and $R^9$ are hydrogen.

4. The compound according to claim 1 having the formula (I-B):

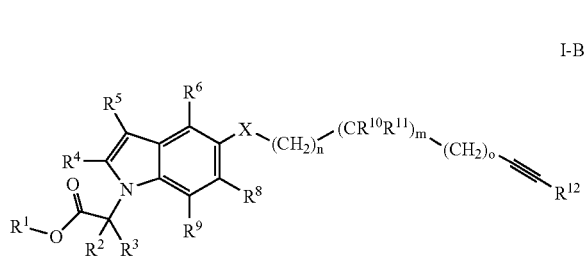

wherein:
X, $R^1$ to $R^5$, $R^{10}$ to $R^{12}$, m, n and o are as defined herein before;
$R^6$, $R^8$ and $R^9$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, fluoro-$C_{1-7}$-alkoxy, cyano-$C_{1-7}$-alkyl and cyano; and
pharmaceutically acceptable salts and/or esters thereof.

5. The compound according to claim 1, wherein $R^6$, $R^8$ and $R^9$ are hydrogen.

6. The compound according to claim 1 having the formula (I-C):

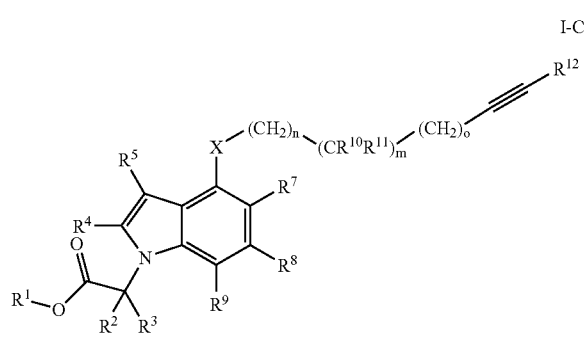

wherein:
X, $R^1$ to $R^5$, $R^{10}$ to $R^{12}$, m, n and o are as defined herein before;
$R^7$, $R^8$ and $R^9$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, fluoro-$C_{1-7}$-alkoxy, cyano-$C_{1-7}$-alkyl and cyano; and
pharmaceutically acceptable salts and/or esters thereof.

7. The compound according to claim 1, wherein $R^7$, $R^8$ and $R^9$ are hydrogen.

8. The compound according to claim 1 having the formula (I-D):

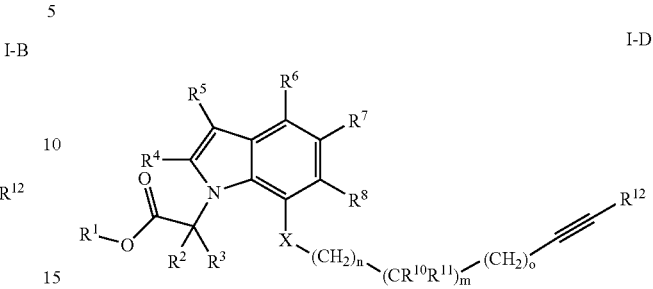

wherein:
X, $R^1$ to $R^5$, $R^{10}$ to $R^{12}$, m, n and o are as defined herein before;
$R^6$, $R^7$ and $R^8$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, fluoro-$C_{1-7}$-alkoxy, cyano-$C_{1-7}$-alkyl and cyano; and
pharmaceutically acceptable salts and/or esters thereof.

9. The compound according to claim 1, wherein $R^6$, $R^7$ and $R^8$ are hydrogen.

10. The compound according to claim 1, wherein $R^1$ is hydrogen.

11. The compound according to claim 1, wherein $R^2$ and $R^3$ independently from each other are hydrogen or methyl.

12. The compound according to claim 1, wherein $R^4$ is hydrogen.

13. The compound according to claim 1, wherein $R^5$ is hydrogen, $C_{1-7}$-alkyl or halogen.

14. The compound according to claim 1, wherein X is S, O or $NR^{13}$ and wherein $R^{13}$ is hydrogen, $C_{1-7}$-alkyl, $C_{3-7}$-cycloalkyl, fluoro-$C_{1-7}$-alkyl, hydroxy-$C_{2-7}$-alkyl, or $C_{1-7}$-alkoxy-$C_{2-7}$-alkyl.

15. The compound according to claim 1, wherein X is O.

16. The compound according to claim 1, wherein X is $(CH_2)_p NR^{13} CO$ or $(CH_2)_p CONR^{13}$ and wherein $R^{13}$ is selected from hydrogen, $C_{1-7}$-alkyl, $C_{3-7}$-cycloalkyl, fluoro-$C_{1-7}$-aklyl, hydroxy-$C_{2-7}$-alkyl, or $C_{1-7}$-alkoxy-$C_{2-7}$-alkyl and p is 0, 1 or 2.

17. The compound according to claim 1, wherein m is 0.

18. The compound according to claim 17, wherein m is 0 and the sum of n and o is 1, 2 or 3.

19. The compound according to claim 17, wherein the sum of n and o is 2 or 3.

20. The compound according to claim 1, wherein $R^{12}$ is unsubstituted phenyl or phenyl substituted with one to three groups selected from $C_{1-7}$-alkyl, $C_{1-7}$-alkoxy, halogen, fluoro-$C_{1-7}$-alkyl, fluoro-$C_{1-7}$-alkoxy and cyano.

21. The compound according to claim 1, wherein $R^{12}$ is phenyl substituted with halogen, $C_{1-7}$-alkoxy, fluoro-$C_{1-7}$-alkyl or fluoro-$C_{1-7}$-alkoxy.

22. The compound according to claim 1, selected from the group consisting of:

{6-[5-(4-trifluoromethoxy-phenyl)-pent-4-ynyloxy]-indol-1-yl}-acetic acid,
{6-[5-(3-trifluoromethoxy-phenyl)-pent-4-ynyloxy]-indol-1-yl}-acetic acid,
{6-[5-(4-trifluoromethyl-phenyl)-pent-4-ynyloxy]-indol-1-yl}-acetic acid,
{6-[5-(3-trifluoromethyl-phenyl)-pent-4-ynyloxy]-indol-1-yl}-acetic acid,
{4-[5-(4-trifluoromethoxy-phenyl)-pent-4-ynyloxy]-indol-1-yl}-acetic acid,
{5-[5-(4-trifluoromethoxy-phenyl)-pent-4-ynyloxy]-indol-1-yl}-acetic acid,
{6-[2,2-dimethyl-5-(4-trifluoromethoxy-phenyl)-pent-4-ynyloxy]-indol-1-yl}-acetic acid,
(6-{methyl-[5-(3-trifluoromethoxy-phenyl)-pent-4-ynoyl]-amino}-indol-1-yl)-acetic acid,
{6-[5-(4-trifluoromethoxy-phenyl)-pent-4-ynylamino]-indol-1-yl}-acetic acid,
(6-{methyl-[5-(4-trifluoromethoxy-phenyl)-pent-4-ynoyl]-amino}-indol-1-yl)-acetic acid,
{7-[5-(4-trifluoromethoxy-phenyl)-pent-4-ynyloxy]-indol-1-yl}-acetic acid,
[rac]-2-{6-[5-(4-trifluoromethoxy-phenyl)-pent-4-ynyloxy]-indol-1-yl}-propionic acid,
(6-{[3-(4-trifluoromethoxy-phenyl)-prop-2-ynylcarbamoyl]-methyl}-indol-1-yl)-acetic acid,
(6-{[3-(4-trifluoromethyl-phenyl)-prop-2-ynylcarbamoyl]-methyl}-indol-1-yl)-acetic acid,
[6-({methyl-[5-(4-trifluoromethyl-phenyl)-pent-4-ynoyl]-amino}-methyl)-indol-1-yl]-acetic acid,
[6-({methyl-[3-(4-trifluoromethoxy-phenyl)-prop-2-ynyl]-carbamoyl}-methyl)-indol-1-yl]-acetic acid,
[rac]-{6-[1-methyl-5-(4-trifluoromethoxy-phenyl)-pent-4-ynyloxy]-indol-1-yl}-acetic acid, and pharmaceutically acceptable salts and/or esters thereof.

23. The compound according to claim 1, selected from the group consisting of:

{6-[5-(4-trifluoromethoxy-phenyl)-pent-4-ynyloxy]-indol-1-yl}-acetic acid,
{6-[5-(4-trifluoromethyl-phenyl)-pent-4-ynyloxy]-indol-1-yl}-acetic acid,
{5-[5-(4-trifluoromethoxy-phenyl)-pent-4-ynyloxy]-indol-1-yl}-acetic acid,
{6-[5-(4-trifluoromethoxy-phenyl)-pent-4-ynylamino]-indol-1-yl}-acetic acid,
(6-{methyl-[5-(4-trifluoromethoxy-phenyl)-pent-4-ynoyl]-amino}-indol-1-yl)-acetic acid,
2-{6-[5-(4-trifluoromethoxy-phenyl)-pent-4-ynyloxy]-indol-1-yl}-propionic acid,
[rac]-{6-[1-methyl-5-(4-trifluoromethoxy-phenyl)-pent-4-ynyloxy]-indol-1-yl}-acetic acid, and pharmaceutically acceptable salts and/or esters thereof.

24. A process for the manufacture of a compound according to claim 1, comprising the steps of:

a) reacting a compound of formula

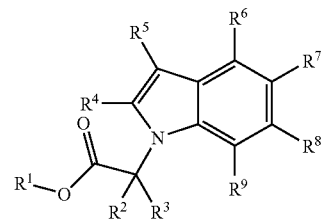

II wherein $R^1$ is $C_{1-7}$-alkyl, $R^2$ to $R^9$ are as defined in claim 1 and one of $R^6$, $R^7$, $R^8$ or $R^9$ is selected from —OH, —SH or —NHR$^{13}$, wherein $R^{13}$ is as defined in claim 1, with a compound of formula

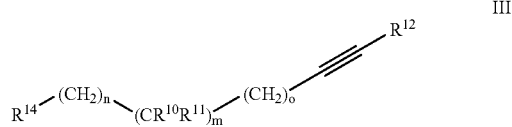

III wherein $R^{10}$, $R^{11}$, $R^{12}$ n, m and o are as defined in claim 1 and $R^{14}$ is —OH, —Cl, —Br, —I or another leaving group, to obtain a compound of formula

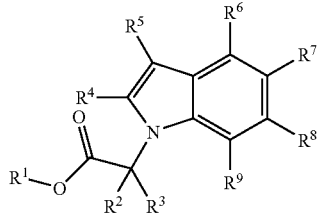

I-1 wherein one of $R^6$, $R^7$, $R^8$ and $R^9$ is

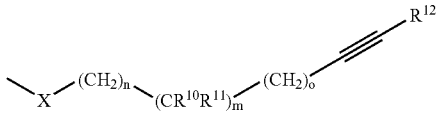

and wherein X is O, S, or —NR$^{13}$, $R^1$ is $C_{1-7}$-alkyl and $R^2$ to $R^{13}$ are as defined in claim 1, and optionally hydrolyzing the ester group to obtain a compound of formula I, wherein $R^1$ is hydrogen;

or, alternatively, b) reacting a compound of formula

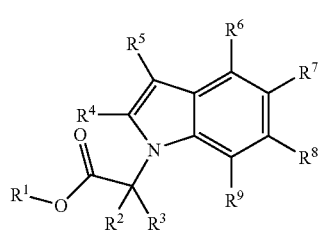

IV wherein $R^1$ is $C_{1-7}$-alkyl, $R^2$ to $R^9$ are as defined in claim 1 and one of $R^6$, $R^7$, $R^8$ or $R^9$ is —$(CH_2)_p$—$NHR^{13}$, wherein $R^{13}$ and p are as defined in claim 1, with a compound of formula

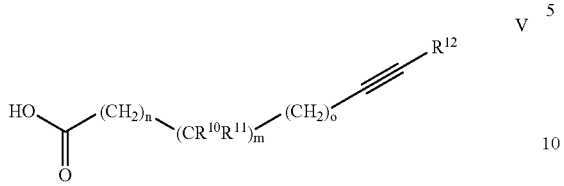
V wherein $R^{10}$, $R^{11}$, $R^{12}$, m, n and o are as defined in claim 1, to obtain a compound of formula

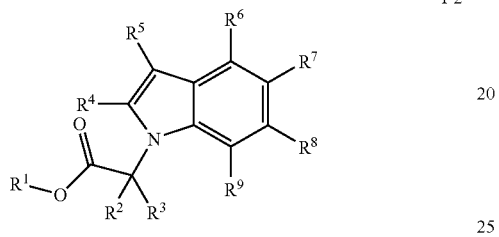
I-2 wherein one of $R^6$, $R^7$, $R^8$ and $R^9$ is

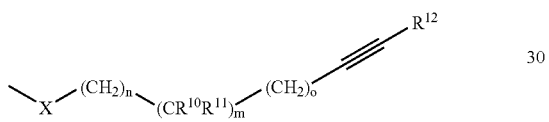

and wherein X is —$(CH_2)_p$—$NR^{13}CO$—, $R^1$ is $C_{1-7}$-alkyl and $R^2$ to $R^{13}$ and m, n, o and p are as defined in claim 1,
and optionally hydrolyzing the ester group to obtain a compound of formula I, wherein $R^1$ is hydrogen;
or, alternatively,
c) reacting a compound of formula

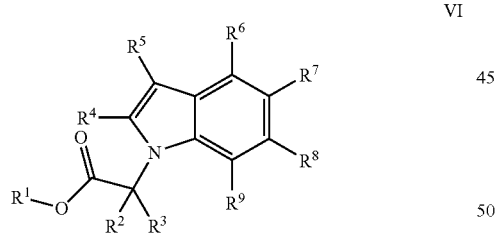
VI wherein $R^1$ is $C_{1-7}$-alkyl, $R^2$ to $R^9$ are as defined in claim 1 and one of $R^6$, $R^7$, $R^8$ or $R^9$ is —$(CH_2)_p$—COOH, and p is defined as defined in claim 1,
with a compound of formula

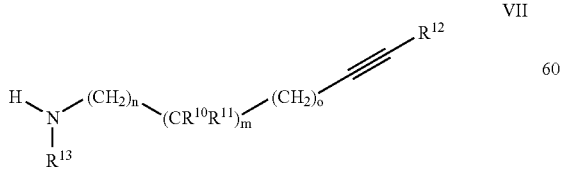
VII wherein $R^{10}$, $R^{11}$, $R^{12}$, $R^{13}$, m, n and o are as defined in claim 1, to obtain a compound of formula

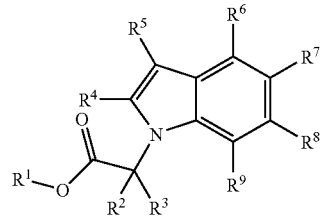
I-3 wherein one of $R^6$, $R^7$, $R^8$ and $R^9$ is

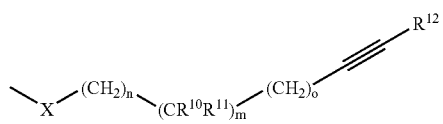

and wherein X is —$(CH_2)_p$—$CONR^{13}$, $R^1$ is $C_{1-7}$-alkyl and $R^2$ to $R^{13}$ and m, n, o and p are as defined in claim 1,
and optionally hydrolyzing the ester group to obtain a compound of formula I, wherein $R^1$ is hydrogen;
or, alternatively,
d) reacting a compound of formula

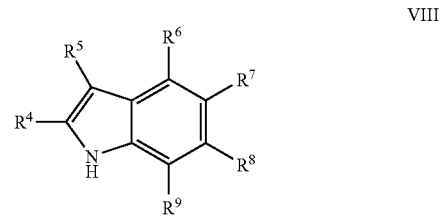
VIII wherein $R^4$ to $R^9$ are as defined in claim 1, with a compound of formula

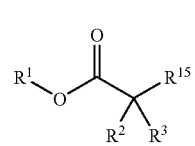
IX wherein $R^1$ is $C_{1-7}$-alkyl, $R^2$ and $R^3$ are as defined in claim 1 and $R^{15}$ is halogen, triflate or another leaving group, to obtain a compound of formula

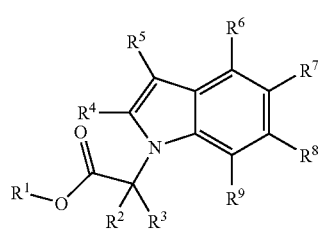
I wherein $R^1$ is $C_{1-7}$-alkyl and $R^2$ to $R^9$ are as defined in claim 1,
and optionally hydrolyzing the ester group to obtain a compound of formula I, wherein $R^1$ is hydrogen.

25. A pharmaceutical composition comprising a therapeutically effective amount of a compound of claim 1 as well as a pharmaceutically acceptable carrier and/or adjuvant.

* * * * *